United States Patent
Hocek et al.

(10) Patent No.: US 10,730,905 B2
(45) Date of Patent: Aug. 4, 2020

(54) SUBSTITUTED HETEROPENTADIENO-PYRROLOPYRIMIDINE RIBONUCLEOSIDES FOR THERAPEUTIC USE

(71) Applicants: USTAV ORGANICKE CHEMIE A BIOCHEMIE AV CR, V.V.I., Prague (CZ); UNIVERZITA PALACKEHO V OLOMOUCI, Olomouc (CZ)

(72) Inventors: Michal Hocek, Prague (CZ); Anna Tokarenko, Ivano-Frankivsk (UA); Sabina Smolen, Pawonkow (PL); Marian Hajduch, Moravsky Beroun (CZ); Petr Dzubak, Brodek u Prerova (CZ)

(73) Assignees: USTAV ORGANICKE CHEMIE A BIOCHEMIE AV CR, V.V.I., Prague (CZ); UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 16/308,796

(22) PCT Filed: Jul. 31, 2017

(86) PCT No.: PCT/CZ2017/050031
§ 371 (c)(1),
(2) Date: Dec. 10, 2018

(87) PCT Pub. No.: WO2018/024265
PCT Pub. Date: Feb. 8, 2018

(65) Prior Publication Data
US 2019/0144486 A1 May 16, 2019

(30) Foreign Application Priority Data
Aug. 2, 2016 (CZ) .................... 2016-465

(51) Int. Cl.
| | |
|---|---|
| A61K 31/519 | (2006.01) |
| A61K 31/4985 | (2006.01) |
| A61K 31/407 | (2006.01) |
| A61K 31/341 | (2006.01) |
| C07D 487/16 | (2006.01) |
| C07D 487/14 | (2006.01) |
| C07D 491/14 | (2006.01) |
| C07D 491/16 | (2006.01) |
| C07H 19/23 | (2006.01) |
| A61P 35/02 | (2006.01) |
| C07H 19/24 | (2006.01) |

(52) U.S. Cl.
CPC .............. *C07H 19/23* (2013.01); *A61P 35/02* (2018.01); *C07H 19/24* (2013.01)

(58) Field of Classification Search
CPC .............. A61K 31/4985; A61K 31/407; C07D 487/16; C07D 487/14; C07D 491/14; C07D 491/16; C07H 19/23; A61P 35/02
USPC .......... 514/36, 267, 411, 468; 544/251, 250; 548/429, 430; 549/458
See application file for complete search history.

(56) References Cited

FOREIGN PATENT DOCUMENTS

| WO | 2009089804 A1 | 7/2009 |
| WO | 2010121576 A1 | 10/2010 |

OTHER PUBLICATIONS

Golub et al., "Molecular classification of Cancer: Class discovery and class prediction by gene expression monitoring", Science (1999), 286: pp. 531-538. (Year: 1999).*
Lala, P. and A. Orucevic, "Role of nitric oxide in tumor progression: Lessons from experimental tumors", Cancer and Meta. Rev. (1998), 17: pp. 91-106. (Year: 1998).*
Schram, K. and L. Townsend, "Pyrrolopyrimidine nucleosides. Part XI. Influence of amino-groups at C-4 and C-6 or an amino-group at C6 on the reactivity of a 5-cyano-group in pyrrolo[2,3-d]pyrimidine nucleosides", J. Chem. Soc., Perkin Trans. 1 (1975), 13: pp. 1253-1257. (Year: 1975).*
Tichy Michal et al, "Synthesis and biological activity of benzo-fused 7-deazaadenosine analogues. 5- and 6-substituted 4-amino- or 4-alkylpyrimido[4,5-b]indole ribonucleosides", Bioorganic & Medicinal Chemistry, vol. 21, No. 17, Jun. 17, 2013 (Jun. 17, 2013), pp. 5362-5372.
Michal Tichy et al, "Synthesis and Cytostatic and Antiviral Profiling of Thieno-Fused 7-Deazapurine Ribonucleosides", Journal of Medicinal Chemistry, vol. 60, No. 6, Feb. 21, 2017 (Feb. 21, 2017), pp. 2411-2424.
International Search Report and Written Opinion for corresponding PCT application No. PCT/CZ2017/050031, dated Oct. 30, 2017.

* cited by examiner

*Primary Examiner* — Matthew P Coughlin
*Assistant Examiner* — Sagar Patel
(74) *Attorney, Agent, or Firm* — Notaro, Michalos & Zaccaria P.C.

(57) ABSTRACT

Substituted heteropentadieno-pyrrolopyrimidine ribonucleosides of general formula I, where R is selected from the group comprising furan-2-yl, furan-3-yl, benzofuran-2-yl, methylsulfanyl, methoxy, amino, dimethylamino, methyl or chloro, and pharmaceutically acceptable salt thereof, their optical isomers and mixtures of such optical isomers.

8 Claims, No Drawings

SUBSTITUTED HETEROPENTADIENO-PYRROLOPYRIMIDINE RIBONUCLEOSIDES FOR THERAPEUTIC USE

FIELD OF THE INVENTION

The invention provides a new type of compounds with anti-cancer activity as well as their therapeutic use.

BACKGROUND OF THE INVENTION

Despite the existence of tens of approved antiproliferative drugs, the treatment of many kinds of leukemia and other cancers is still not very successful. In addition, current drugs often have significant adverse effects. Thus the development of a new type of compounds with anti-cancer properties is needed.

Recently, our group discovered, patented and published two new classes of cytostatic compounds, 7-(het)aryl-7-deazaadenosines (formula A, WO2010121576; Bourderioux, A. et al., *J. Med. Chem.* 2011, 54, 5498-5507) and 6-hetaryl-7-deazapurine ribonucleosides bearing hydrogen or fluorine in position 7 (formula B, WO2009089804; Nauš, P. et al., *J. Med. Chem.* 2010, 53, 460-470).

Pyrimidoindole ribonucleosides and 8H-thieno[2',3':4,5]pyrrolo[2,3-d]pyrimidine ribonucleosides prepared in our group are the only known types of annulated deazapurine nucleosides (formula C, ref.: Tichý, M. et al., *Bioorg. Med. Chem.* 2012, 20, 6123-6133; Tichý, M. et al., *Bioorg. Med. Chem.* 2013, 21, 5362-5372; Tichý, M. et al., *J. Med. Chem.* 2017, 60, 2411-2424).

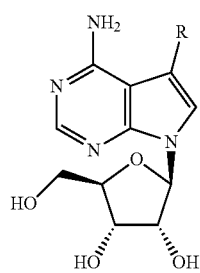

(A)

R = aryl, heteroaryl

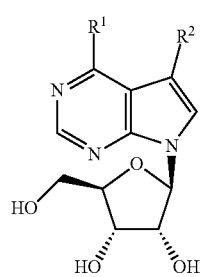

(B)

$R^1$ = aryl, heteroaryl
$R^2$ = H, halo, heteroaryl

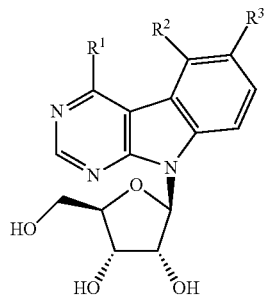

(C)

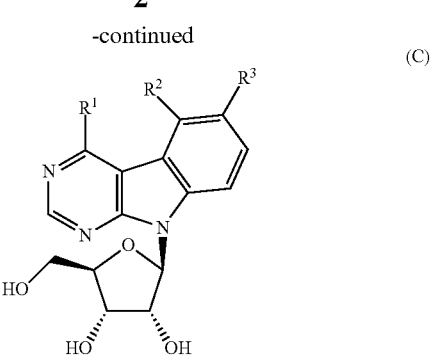

$R^1$ = NH$_2$, Me, MeNH$_2$, Me$_2$NH, cyklopropyl, heteroaryl, aryl
$R^2$ = H, Cl, heteroaryl
$R^3$ = H, Cl, heteroaryl

SUMMARY OF THE INVENTION

This invention describes new 4-substituted heteropentadieno-pyrrolopyrimidine ribonucleosides of general formula I, exhibiting strong cytostatic and cytotoxic effects on cell lines preferentially of tumor origin and on broad spectrum of cancers of various histogenetic origin.

The specific fused heterocyclic structure bonded at positions 7 and 8 of the deazapurine skeleton, carrying heteroatoms at specific ring positions makes these compounds significantly different from all previously prepared 7-deazapurine derivatives of general formulas A and B as well as from pyrimidoindole ribonucleosides of general formula C. Heteropentadieno-pyrrolopyrimidine ribonucleosides presented herein are a new class of compounds, which was not described previously. These compounds are unknown in nature and have not been synthesized yet. Hence, their biological activity has not yet been studied either. Heteropentadieno-pyrrolopyrimidine ribonucleosides mentioned above are a new and unique type of nucleosides with a rigid tricyclic base, which leads to a new type of interaction with biological systems and therefore presumably to a different mechanism of action than other 7-substituted 7-deazapurine nucleosides exhibit.

The object of the presented invention is substituted heteropentadieno-pyrrolopyrimidine ribonucleosides of general formula I:

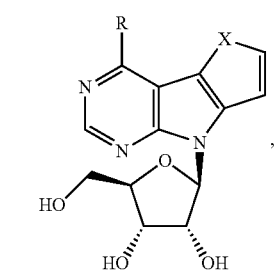

(I)

wherein
R is selected from the group comprising
C1-C5 alkyl, optionally substituted by at least one substitutent selected from hydroxy, sulfanyl, amino, C1-C5 alkoxy, C1-C5 sulfanyl, C1-C5 alkylamino, di(C1-C5 alkyl)amino;

C2-C6 alkenyl, optionally substituted by at least one substitutent selected from hydroxy, sulfanyl, amino, C1-C5 alkoxy, C1-C5 sulfanyl, C1-C5 alkylamino, di(C1-C5 alkyl)amino;

C6-C12 aryl, optionally substituted by at least one substitutent selected from C1-C5 alkyl, hydroxy, sulfanyl, amino, C1-C5 alkoxy, C1-C5 sulfanyl, C1-C5 alkylamino, di(C1-C5 alkyl)amino;

C4-12 heteroaryl, comprising at least one O atom; optionally substituted by at least one substitutent selected from C1-C5 alkyl, hydroxy, sulfanyl, amino, C1-C5 alkoxy, C1-C5 sulfanyl, C1-C5 alkylamino, di(C1-C5 alkyl)amino;

amino,
C1-C5 alkylamino,
di(C1-C5 alkyl)amino,
C1-C5 alkoxy,
C1-C5 alkylsulfanyl,
halogeno;

—X— is selected from —O—, —NH— or —N(C1-C5 alkyl)- group;

and pharmaceutically acceptable salt thereof, their optical isomers and mixtures of such optical isomers including racemic mixtures.

In one preferred embodiment, R is selected from the group comprising C1-C5 alkyl, phenyl, naphthyl, 2-furyl, 3-furyl, benzofuryl, dibenzofuryl, C1-C5 alkylsulfanyl, amino, C1-C5 alkylamino, di(C1-C5 alkyl)amino, C1-C5 alkoxy, halogeno group.

More preferably, R is selected from the group comprising furan-2-yl, furan-3-yl, benzofuran-2-yl, methylsulfanyl, methoxy, amino, dimethylamino, methyl or chloro.

As described herein and unless otherwise indicated, the individual substituents have the following meanings:

alkyl is a linear or branched hydrocarbon chain containing the number of carbons indicated at the place of use of the term;

alkenyl means a straight or branched chain hydrocarbon chain containing one or more double bonds and containing the number of carbon atoms indicated at the place of use of that term;

aryl is a hydrocarbon chain comprising at least one aromatic ring and containing the number of carbons indicated at the place of use of the term. The aryl may also contain more than one aromatic ring, then these rings may be condensed or non-fused;

heteroaryl is a hydrocarbon group containing at least one heteroatom and at least one aromatic ring; The number of carbons and the number and type of heteroatom being indicated at the place of use of the term. Heteroaryl may also contain more than one aromatic ring, then these rings may be condensed or non-fused;

hydroxy denotes —OH;
sulfanyl denotes —SH;
amino denotes —NH$_2$;

alkylamino is a group formed by the substitution of one or two hydrogen atoms of an amino group by the above-defined alkyl;

dialkylamino is a group formed by the substitution of the two hydrogen atoms of an amino group by the two alkyl groups defined above, which are the same or different;

alkoxy refers to a group —OR', where R' corresponds to the definition of alkyl;

alkylsulfanyl represents a group —SR', where R' corresponds to the definition of alkyl;

halogeno means fluoro, chloro, bromo or iodo, preferably chloro.

As used herein, the term "pharmaceutically acceptable salts" refers to salts that retain the biological effectiveness and properties of the claimed compounds of general formula I according to this invention, and which are within reasonable medical judgment suitable for use in contact with the tissues of humans and lower animals without undue toxicity, irritation, allergic reactions, and the like, and have an acceptable benefit/risk ratio. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in Remington's Pharmaceutical Sciences, 20th ed., Mack Publishing Company, Easton, Pa., (1985), which is herein incorporated by reference.

In a preferred embodiment, the present invention provides 4-substituted heteropentadieno-pyrrolopyrimidine ribonucleosides of general formula I, being:

4-methyl-8-(β-D-ribofuranosyl)-8H-furo[2',3':4,5]pyrrolo[2,3-d]pyrimidine, 4-methoxy-8-(β-D-ribofuranosyl)-8H-furo[2',3':4,5]pyrrolo[2,3-d]pyrimidine, 4-(methylsulfanyl)-8-(β-D-ribofuranosyl)-8H-furo[2',3':4,5]pyrrolo[2,3-d]pyrimidine, 8-(β-D-ribofuranosyl)-8H-furo[2',3':4,5]pyrrolo[2,3-d]pyrimidin-4-amine, 4-(furan-2-yl)-8-(β-D-ribofuranosyl)-8H-furo[2',3':4,5]pyrrolo[2,3-d]pyrimidine, 4-(furan-3-yl)-8-(β-D-ribofuranosyl)-8H-furo[2',3':4,5]pyrrolo[2,3-d]pyrimidine, 4-(benzofuran-2-yl)-8-(β-D-ribofuranosyl)-8H-furo[2',3':4,5]pyrrolo[2,3-d]pyrimidine,
N,N-dimethyl-8-(β-D-ribofuranosyl)-8H-furo[2',3':4,5]pyrrolo[2,3-d]pyrimidin-4-amine,
4,5-dimethyl-8-(β-D-ribofuranosyl)-5,8-dihydropyrrolo[2',3':4,5]pyrrolo[2,3-d]pyrimidine,
4-methoxy-5-methyl-8-(β-D-ribofuranosyl)-5,8-dihydropyrrolo[2',3':4,5]pyrrolo[2,3-d]pyrimidine,
5-methyl-4-(methylsulfanyl)-8-(β-D-ribofuranosyl)-5,8-dihydropyrrolo[2',3':4,5]pyrrolo[2,3-d]pyrimidine,
5-methyl-8-(β-D-ribofuranosyl)-5,8-dihydropyrrolo[2',3':4,5]pyrrolo[2,3-d]pyrimidin-4-amine,
4-(furan-2-yl)-5-methyl-8-(β-D-ribofuranosyl)-5,8-dihydropyrrolo[2',3':4,5]pyrrolo[2,3-d]pyrimidine,
4-(furan-3-yl)-5-methyl-8-(β-D-ribofuranosyl)-5,8-dihydropyrrolo[2',3':4,5]pyrrolo[2,3-d]pyrimidine,
4-(benzofuran-2-yl)-5-methyl-8-(β-D-ribofuranosyl)-5,8-dihydropyrrolo[2',3':4,5]pyrrolo[2,3-d]pyrimidine,
N,N,5-trimethyl-8-(β-D-ribofuranosyl)-5,8-dihydropyrrolo[2',3':4,5]pyrrolo[2,3-d]pyrimidin-4-amine,
4-chloro-5-methyl-8-(β-D-ribofuranosyl)-5,8-dihydropyrrolo[2',3':4,5]pyrrolo[2,3-d]pyrimidine.

Additionally, the present invention provides 4-substituted heteropentadieno-pyrrolopyrimidine ribonucleosides of general formula I for use as a medicaments.

Present invention provides 4-substituted heteropentadieno-pyrrolopyrimidine ribonucleosides of general formula I for use in inhibition of pathological cell proliferation of tumor/non-tumor/cancer origin and for treatment of tumor/non-tumor/cancer disease associated with cell hyperproliferation.

Present invention provides 4-substituted heteropentadieno-pyrrolopyrimidine ribonucleosides of general formula I for use in treatment of tumor/cancer diseases, covering epithelial, mesenchymal and neuroectoderm origin tumors.

Present invention provides 4-substituted heteropentadieno-pyrrolopyrimidine ribonucleosides of formula I for use the preparation of a medicament for treatment of tumor/cancer diseases, covering e.g. epithelial, mesenchymal and neuroectoderm origin tumors.

Present invention provides a pharmaceutical composition comprising a therapeutically effective amount of a compound of general formula I and one or more pharmaceutically acceptable carriers, excipients/diluents.

The invention also provides the pharmaceutical composition mentioned above for use in inhibition of pathological cell proliferation of tumor/non-tumor/cancer origin and/or for treatment of tumor/non tumor/cancer disease associated with cell hyperproliferation. Cancer diseases include, but are not limited to, adenocarcinoma, lung carcinoma, colon carcinoma, head and neck carcinomas, GIT cancers, liver and pancreatic cancers, breast cancer, ovaria cancer, bladder cancer, bone cancer, brain tumors, cervical cancers, colorectal cancer, prostate cancer, kidney cancer, thyroid cancer, uterine cancer, soft tissue cancer, lymphoma, melanoma, osteosarcoma, leukemias.

The term "therapeutically effective amount" of a compound of the present invention refers to an amount of the compound or drug that is effective in treating a disease or disorder in a human or mammal. In the case of cancer treatment the "effective amount" refers to the amount that inhibits or reduces proliferation of cancer cells, reduces the primary tumor/cancer size, inhibits (that is, to a certain extent slow down and preferably stop) cancer cell infiltration into peripheral organs, inhibits (that is, to a certain extent slow down and preferably stop) the formation of tumor metastases, inhibits, to a certain extent, tumor growth and/or relieves at least to some extent one or more symptoms associated with tumor or cancer. Whereas the drug can prevent growth and/or kill existing cancer cells, it can be cytostatic and/or cytotoxic.

The term "pharmaceutical composition" refers to the formulation of a compound and medium, generally accepted in the art, for the delivery of a biologically active compound to a mammal, e.g., a human. Such a medium includes all pharmaceutically acceptable carriers, diluents or excipients.

The term "pharmaceutically acceptable carrier, diluent or filler" as used herein includes, without limitation, any excipient, carrier, glidant, sweetener, preservative, dye, flavor enhancer, surfactant, dispersing agent, suspending agent, isotonic agent, solvent, or emulsifier that has been approved for use in humans or domestic animals.

The invention further relates to compounds of formula I for use as an active ingredient in a pharmacologically acceptable composition which may be prepared by conventional methods known in the art, e.g., the active ingredient may be in admixture with pharmaceutically acceptable inert organic and/or inorganic carriers and/or with auxiliaries or, where appropriate, attached to them.

The invention also relates to compounds of the formula I for use as second or other active substances having synergistic effect with other active substances in known drugs, or the administration of the compounds of the formula I together with these drugs.

In one embodiment, the present invention also relates to the use of compounds of formula I as prodrugs or other suitable forms which release the active ingredient in vivo.

EXAMPLES

Compounds Numbering

Following numbering of compounds is used, where
ribonucleosides having X=O are designated as 1a-h,
ribonucleosides having X=an =N—CH$_3$ group are designated as 2a-i:

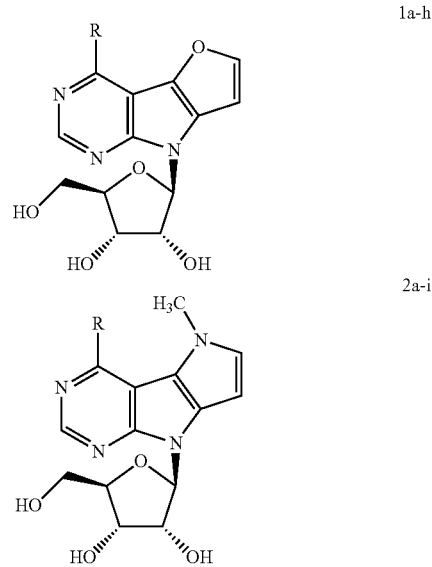

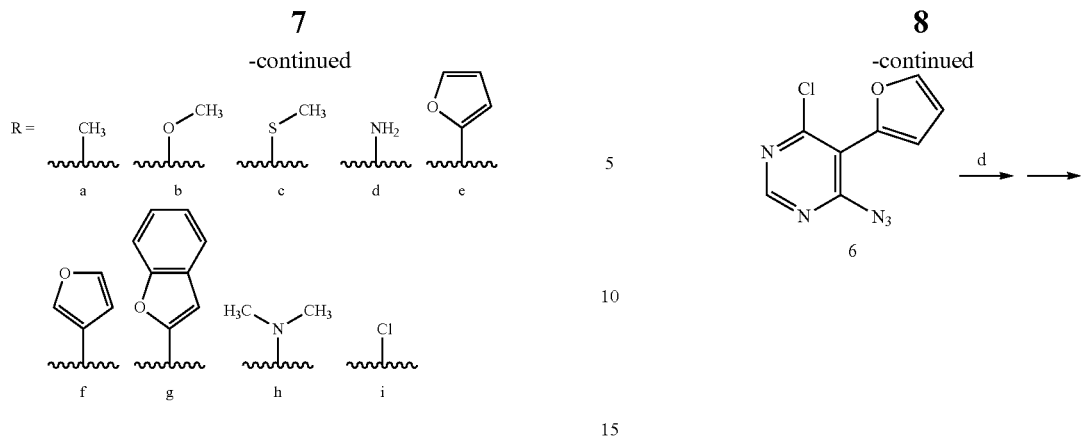

Synthesis of Compounds

The key benzoylated 4-chlorofuropyrrolopyrimidine ribonucleoside was synthesized in 5-step synthesis (Scheme 1), starting from 4,6-dichloropyrimidine (3), which was zincated (compound 4 was not isolated) (Mosrin, M.; Knochel; *Chem. Eur. J.* 2009, 15, 1468-1477) and then coupled with 2-iodofuran furnishing 4,6-dichloro-5-(furan-2-yl)pyrimidine (5) in a good yield (46%). 2-Iodofuran was prepared according to the published procedure (L. Brandsma, H. Verkruijsse *Preparative Polar Organometallic Chemistry*, Springer, Berlin 1987, vol. 1, pp 135-136). Next, the azido group was introduced into position 4 of compound 5 by nucleophilic substitution with NaN$_3$. Photocyclization of obtained 4-azido-6-chloro-5-(furan-2-yl)pyrimidine (6) led to the formation of furopyrrolopyrimidine 7. Tricyclic nucleobase 7 was then converted to nucleoside 8 under Vorbrüggen conditions.

Scheme 1: Synthesis of benzoylated furopyrrolopyrimidine nucleoside

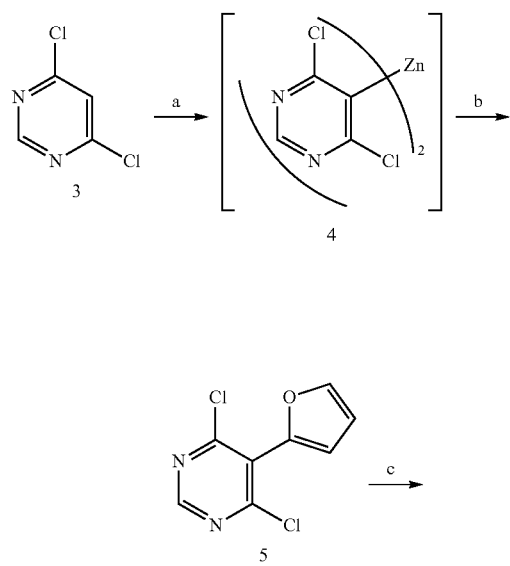

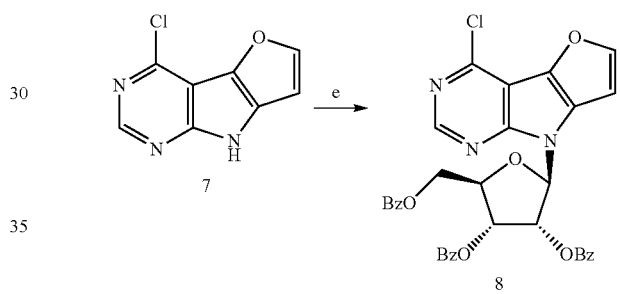

a: (TMP)$_2$Zn·MgCl$_2$·2LiCl, THF, 0° C., 1 h, then r.t., 1 h; b: 2-iodofuran, Pd(PPh$_3$)$_4$, THF, 65° C., 16 h; c: NaN$_3$, LiCl, DMF, r.t.; d: TFA, UV, r.t., 2 days; e: BSA, MeCN, 60° C., 30 min; then 1-O-acetyl-2,3,5-tri-O-benzoyl-β-D-ribofuranose, TMSOTf, 60° C., 4 h.

Desired 4-substituted furopyrrolopyrimidine ribonucleosides were prepared using Pd-catalyzed cross-coupling reactions or nucleophilic substitutions (Scheme 2). 4-Methyl derivative 9a was synthesized by palladium-catalyzed reaction of 4-halogenated nucleoside 8 with trimethylaluminium; subsequent Zemplén deprotection furnished free 4-methyl furopyrrolopyrimidine ribonucleoside 1a. Compounds 1b-d were obtained through nucleophilic substitution at position 4 with sodium methoxide, sodium thiomethoxide or ammonia. In all cases, simultaneous debenzoylation occurs under reaction conditions affording free nucleosides. 4-(Het)aryl furopyrrolopyrimidine ribonucleosides 9e-g were prepared via the Stille or Suzuki-Miyaura cross-coupling reactions. Dimethylamino derivative 9h was synthesized by nucleophilic substitution with dimethylamine. Deprotection of compounds 9e-h by treatment with MeONa in MeOH led to target nucleosides 1e-h.

Scheme 2: Synthesis of 4-substituted furopyrrolopyrimidine nucleosides 9a, e-h and 1a-h

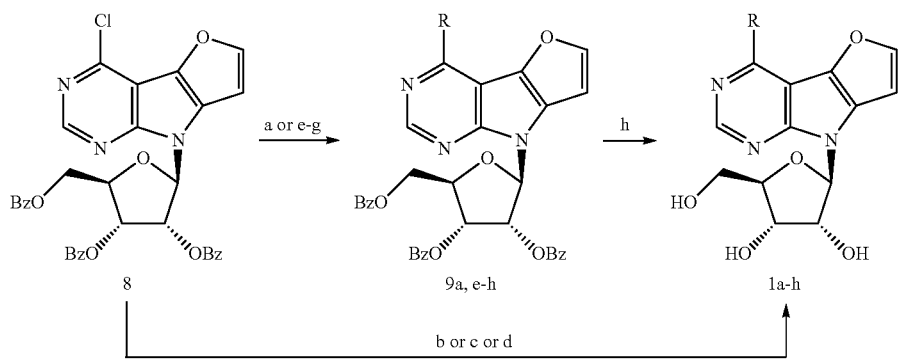

a: Me₃Al, Pd(PPh₃)₄, THF, 70° C., 16 h; b: MeONa, MeOH, r.t., 12 h; c: MeSNa, MeOH, r.t., 12 h; d: NH₃ (aq.), dioxane, 120° C., 16 h; e: 2-tributylstannylfuran, PdCl₂(PPh₃)₂, DMF, 100° C., 1 h; f: R-boronic acid, Pd(PPh₃)₄, K₂CO₃, toluene, 100° C., 6 h; g: Me₂NH in THF, propan-2-ol/EtOH 1:1, r.t., 16 h; h: 1M MeONa in MeOH, MeOH, r.t., 24 h.

The results are presented in Table 1.

TABLE 1

Synthesis of 4-substituted furopyrrolopyrimidine nucleosides 9a, e-h and 1a-h

| Entry | Conditions | R | Protected nucleoside | Yield [%] | Free nucleoside | Yield [%] |
|---|---|---|---|---|---|---|
| 1 | a | Me | 9a | — | 1a | 50 |
| 2 | b | OMe | — | — | 1b | 77 |
| 3 | c | SMe | — | — | 1c | 50 |
| 4 | d | NH₂ | — | — | 1d | 64 |
| 5 | e | 2-furyl | 9e | 81 | 1e | 77 |
| 6 | f | 3-furyl | 9f | 92 | 1f | 81 |
| 7 | f | 2-benzofuryl | 9g | 81 | 1g | 69 |
| 8 | g | NMe₂ | 9h | 61 | 1h | 67 |

The key-intermediate benzoylated 4-chloro-5-methylpyrrolopyrrolopyrimidine ribonucleoside was synthesized starting from 4,6-dichloropyrimidine (3), which was zincated and subsequently coupled with 2-iodo-1-methylpyrrole furnishing 4,6-dichloro-5-(1-methylpyrrol-2-yl)pyrimidine (10) (Scheme 3). 2-Iodo-1-methylpyrrole was prepared by lithiation and subsequent iodination of 1-methylpyrrole according to the published procedure (Mal'kina, A. G. et al.; Synthesis 1996, 5, 589-590). Next, compound 10 was subjected to nucleophilic substitution by one equivalent of sodium azide in DMF to give corresponding azido derivative 11, which was then thermally cyclized to desired 5-methylpyrrolopyrrolopyrimidine 12. Vorbrüggen glycosylation of 12 gave benzoylated 4-chloro-5-methylpyrrolopyrrolopyrimidine nucleoside 13.

Scheme 3: Synthesis of benzoylated 4-chloro-5-methylpyrrolopyrrolopyrimidine nucleoside

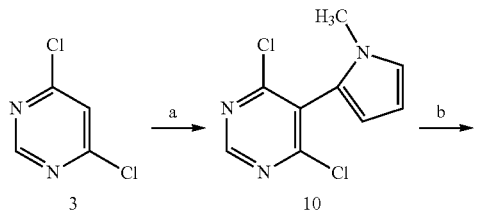

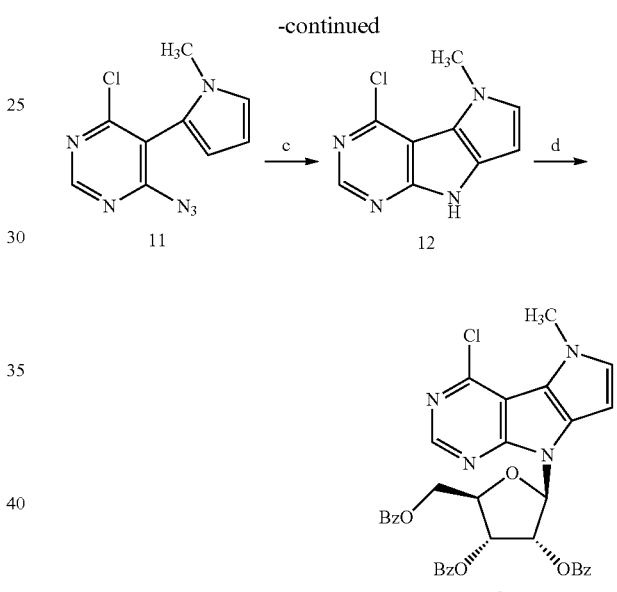

a: 1) (TMP)₂Zn•MgCl₂•2LiCl, THF, 1 h at 0° C., then 1 h at r.t.;
2) 2-iodo-1-methylpyrrole, Pd(PPh₃)₄, THF, 65° C., 16 h; b: NaN₃, LiCl, DMF, r.t., 16 h; c: 1,4-dibromobenzene, 180° C., 30 min; d: 1) BSA, MeCN, r.t., 30 min;
2) 1-O-acetyl-2,3,5-tri-O-benzoyl-b-D-ribofuranose, TMSOTf, 80° C., 3 h.

Target 4-substituted nucleosides were prepared using palladium-catalyzed cross-coupling reactions or nucleophilic substitutions (Scheme 4). Methyl derivative 2a was synthesized by palladium-catalyzed alkylation with trimethylaluminium and subsequent deprotection using sodium methoxide in methanol. Methoxy, methylsulfanyl and amino groups were introduced by nucleophilic substitution reactions, and, under reaction conditions, benzoyl groups were removed furnishing free nucleosides 2b-d, respectively. 4-Hetaryl derivatives 14e-g were synthesized using Stille or Suzuki-Miyaura cross-coupling reactions. 4-Dimethylamino ribonucleoside 14h was prepared by nucleofilic substitution reaction with dimethylamine. Compounds 14e-h were deprotected by sodium methoxide furnishing free nucleosides 2e-h, respectively. Free 4-chloro pyrrolopyrrolopyrimidine ribonucleoside 2i was obtained by treatment of 13 with aqueous ammonia for 1 hour.

Scheme 4: Synthesis of 4-substituted 5-methylpyrrolopyrrolopyrimidine nucleosides 14e-h and 2a-i

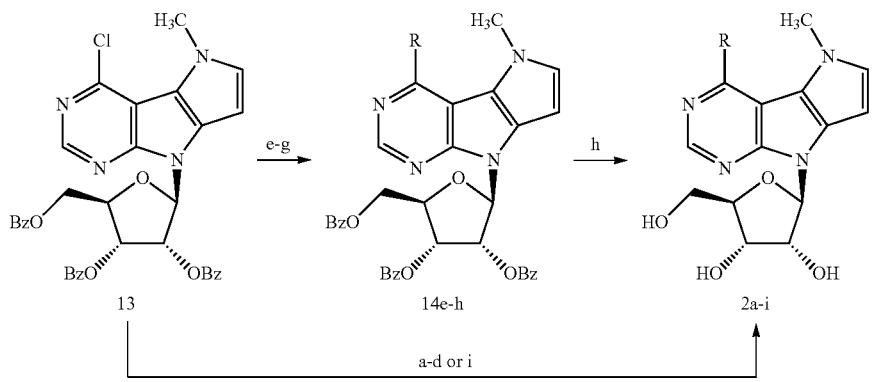

a: Me₃Al, Pd(PPh₃)₄, THF, 70° C., 3 h; then h; b: MeONa, MeOH, r.t., 12 h; c: MeSNa, MeOH, r.t., 12 h;
d: NH₃ (aq.), dioxane, 120° C., 12 h; e: 2-tributylstannylfuran, PdCl₂(PPh₃)₂, DMF, 100° C., 3 h;
f: R-boronic acid, Pd(PPh₃)₄, K₂CO₃, toluene, 100° C., 3 h; g: Me₂NH in THF, isopropanol/THF 2:1, 50° C., 24 h;
h: MeONa, MeOH, r.t., 3 h; i: NH₃ (aq.), dioxane, 100° C., 1 h.

The results are presented in Table 2.

TABLE 2

Synthesis of 4-substituted 5-methylpyrrolopyrrolopyrimidine nucleosides 14e-h and 2a-i

| Entry | Conditions | R | Protected nucleoside | Yield [%] | Free nucleoside | Yield [%] |
|---|---|---|---|---|---|---|
| 1 | a | Me | — | — | 2a | 89 |
| 2 | b | OMe | — | — | 2b | 83 |
| 3 | c | SMe | — | — | 2c | 77 |
| 4 | d | NH₂ | — | — | 2d | 75 |
| 5 | e | 2-furyl | 14e | 95 | 2e | 92 |
| 6 | f | 3-furyl | 14f | 85 | 2f | 83 |
| 7 | f | 2-benzofuryl | 14g | 86 | 2g | 90 |
| 8 | g | NMe₂ | 14h | 75 | 2h | 72 |
| 9 | i | Cl | — | — | 2i | 65 |

EXAMPLES

List of Abbreviations

APCI atmospheric-pressure chemical ionization
aq. aqueous
bd broad doublet
bq broad quartet
bs broad singlet
bt broad triplet
btd broad triplet of doublets
Bz benzoyl
calcd calculated
d doublet
dd doublet of doublets
ddd doublet of doublet of doublets
DMF N,N-dimethylformamide
DMSO dimethylsulfoxide
dt doublet of triplets
EI electron impact
eq. equivalent
ESI electrospray ionization
EtOH ethanol
HPLC high-performance liquid chromatography
HR high resolution
iPr isopropyl
m multiplet
Me methyl
MeCN acetonitrile
MeOH methanol
MeONa sodium methoxide
MeSNa sodium thiomethoxide
m.p. melting point
MS mass spectrometry
NMR nuclear magnetic resonance
Ph phenyl
q quartet
r.t. room temperature
s singlet
SiO₂ silicagel as stationary phase
t triplet
td triplet of doublets
TMSOTf trimethylsilyl trifluoromethansulfonate
TFA trifluoroacetic acid
THF tetrahydrofuran
(TMP)₂Zn bis(2,2,6,6-tetramethypiperidinyl)zinc NMR spectra were recorded on a 400 MHz ($^1$H at 400 MHz, $^{13}$C at 100.6 MHz) or on a 500 MHz ($^1$H at 500 MHz, $^{13}$C at 125.7 MHz) spectrometer. Melting points were determined on a Stuart SMP40 and are uncorrected. Germicid UV bulb, model EUV-13B was used for photocyclization reactions. Optical rotations were measured at 25° C., and $[\alpha]_D^{20}$ values are given in $10^{-1}$ deg cm$^2$ g$^{-1}$. High resolution mass spectra were measured using ESI, EI or APCI techniques. The purity of all tested compounds was confirmed by HPLC analysis and was >95%.

TABLE 3

List of Compounds in Examples

| Example | Compound | Structure | Systematic name |
|---|---|---|---|
| 5 | 1a | (structure shown) | 4-methyl-8-(β-D-ribofuranosyl)-8H-furo[2',3':4,5]pyrrolo[2,3-d]pyrimidine |

TABLE 3-continued

List of Compounds in Examples

| Example | Compound | Structure | Systematic name |
|---|---|---|---|
| 6 | 1b | 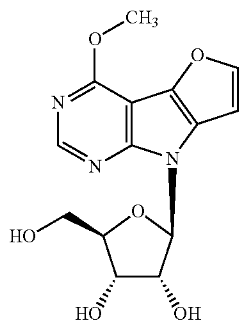 [SMILES: COc1ncnc2c1c1occc1n2[C@@H]1O[C@H](CO)[C@@H](O)[C@H]1O] | 4-methoxy-8-(β-D-ribofuranosyl)-8H-furo[2',3':4,5]pyrrolo[2,3-d]pyrimidine |
| 7 | 1c | 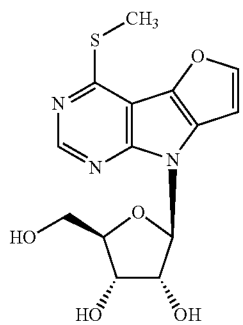 [SMILES: CSc1ncnc2c1c1occc1n2[C@@H]1O[C@H](CO)[C@@H](O)[C@H]1O] | 4-(methylsulfanyl)-8-(β-D-ribofuranosyl)-8H-furo[2',3':4,5]pyrrolo[2,3-d]pyrimidine |
| 8 | 1d | 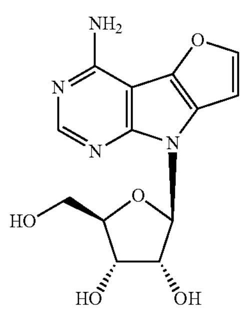 [SMILES: Nc1ncnc2c1c1occc1n2[C@@H]1O[C@H](CO)[C@@H](O)[C@H]1O] | 8-(β-D-ribofuranosyl)-8H-furo[2',3':4,5]pyrrolo[2,3-d]pyrimidin-4-amine |
| 10 | 1e | 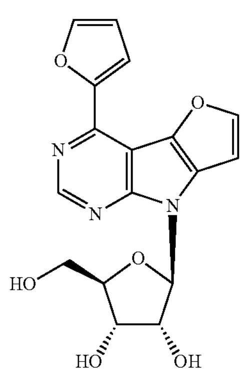 [SMILES: OC[C@H]1O[C@@H](n2c3ccoc3c3c(-c4ccco4)ncnc32)[C@H](O)[C@@H]1O] | 4-(furan-2-yl)-8-(β-D-ribofuranosyl)-8H-furo[2',3':4,5]pyrrolo[2,3-d]pyrimidine |
| 12 | 1f | 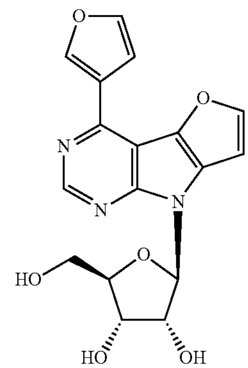 [SMILES: OC[C@H]1O[C@@H](n2c3ccoc3c3c(-c4ccoc4)ncnc32)[C@H](O)[C@@H]1O] | 4-(furan-3-yl)-8-(β-D-ribofuranosyl)-8H-furo[2',3':4,5]pyrrolo[2,3-d]pyrimidine |
| 14 | 1g | 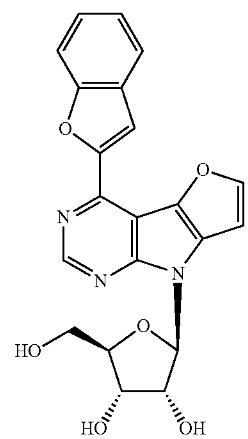 [SMILES: OC[C@H]1O[C@@H](n2c3ccoc3c3c(-c4cc5ccccc5o4)ncnc32)[C@H](O)[C@@H]1O] | 4-(benzofuran-2-yl)-8-(β-D-ribofuranosyl)-8H-furo[2',3':4,5]pyrrolo[2,3-d]pyrimidine |
| 16 | 1h | 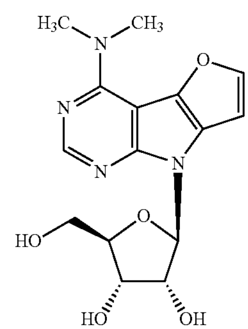 [SMILES: CN(C)c1ncnc2c1c1occc1n2[C@@H]1O[C@H](CO)[C@@H](O)[C@H]1O] | N,N-dimethyl-8-(β-D-ribofuranosyl)-8H-furo[2',3':4,5]pyrrolo[2,3-d]pyrimidin-4-amine |
| 21 | 2a | 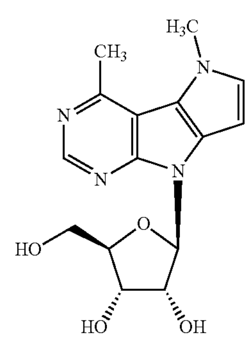 [SMILES: Cc1ncnc2c1c1c(ccn1C)n2[C@@H]1O[C@H](CO)[C@@H](O)[C@H]1O] | 4,5-dimethyl-8-(β-D-ribofuranosyl)-5,8-dihydropyrrolo[2',3':4,5]pyrrolo[2,3-d]pyrimidine |

TABLE 3-continued

List of Compounds in Examples

| Example | Compound | Structure | Systematic name |
|---------|----------|-----------|-----------------|
| 22 | 2b | 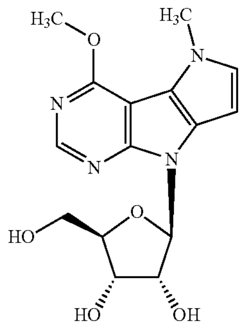 [SMILES: COc1ncnc2c1c1c(ccn1C)n2[C@@H]1O[C@H](CO)[C@@H](O)[C@H]1O] | 4-methoxy-5-methyl-8-(β-D-ribofuranosyl)-5,8-dihydropyrrolo[2',3':4,5]pyrrolo[2,3-d]pyrimidine |
| 23 | 2c | 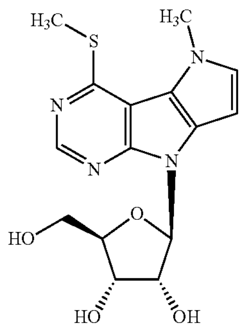 [SMILES: CSc1ncnc2c1c1c(ccn1C)n2[C@@H]1O[C@H](CO)[C@@H](O)[C@H]1O] | 5-methyl-4-(methylsulfanyl)-8-(β-D-ribofuranosyl)-5,8-dihydropyrrolo[2',3':4,5]pyrrolo[2,3-d]pyrimidine |
| 24 | 2d | 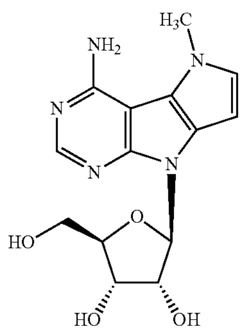 [SMILES: Cn1ccc2c1c1c(N)ncnc1n2[C@@H]1O[C@H](CO)[C@@H](O)[C@H]1O] | 5-methyl-8-(β-D-ribofuranosyl)-5,8-dihydropyrrolo[2',3':4,5]pyrrolo[2,3-d]pyrimidin-4-amine |
| 26 | 2e | 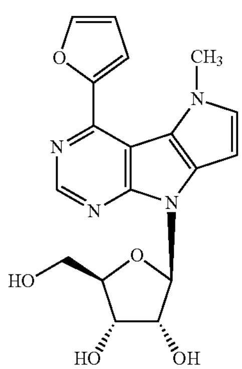 [SMILES: Cn1ccc2c1c1c(-c3ccco3)ncnc1n2[C@@H]1O[C@H](CO)[C@@H](O)[C@H]1O] | 4-(furan-2-yl)-5-methyl-8-(β-D-ribofuranosyl)-5,8-dihydropyrrolo[2',3':4,5]pyrrolo[2,3-d]pyrimidine |
| 28 | 2f | 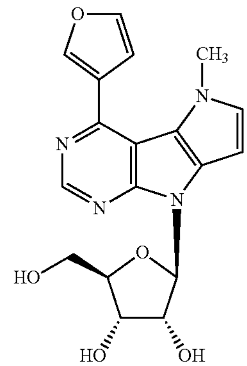 [SMILES: Cn1ccc2c1c1c(-c3ccoc3)ncnc1n2[C@@H]1O[C@H](CO)[C@@H](O)[C@H]1O] | 4-(furan-3-yl)-5-methyl-8-(β-D-ribofuranosyl)-5,8-dihydropyrrolo[2',3':4,5]pyrrolo[2,3-d]pyrimidine |
| 30 | 2g | 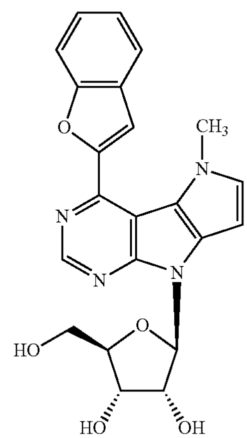 [SMILES: Cn1ccc2c1c1c(-c3cc4ccccc4o3)ncnc1n2[C@@H]1O[C@H](CO)[C@@H](O)[C@H]1O] | 4-(benzofuran-2-yl)-5-methyl-8-(β-D-ribofuranosyl)-5,8-dihydropyrrolo[2',3':4,5]pyrrolo[2,3-d]pyrimidine |
| 32 | 2h | 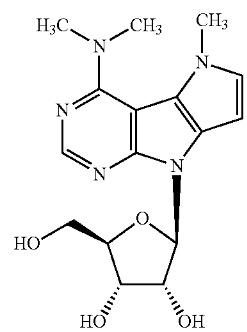 [SMILES: CN(C)c1ncnc2c1c1c(ccn1C)n2[C@@H]1O[C@H](CO)[C@@H](O)[C@H]1O] | N,N,5-trimethyl-8-(β-D-ribofuranosyl)-5,8-dihydropyrrolo[2',3':4,5]pyrrolo[2,3-d]pyrimidin-4-amine |
| 33 | 2i | 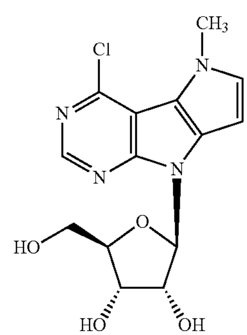 [SMILES: Cn1ccc2c1c1c(Cl)ncnc1n2[C@@H]1O[C@H](CO)[C@@H](O)[C@H]1O] | 4-chloro-5-methyl-8-(β-D-ribofuranosyl)-5,8-dihydropyrrolo[2',3':4,5]pyrrolo[2,3-d]pyrimidine |

General Procedure A (Suzuki-Miyaura Coupling)

Protected nucleoside 8 or 13 (200 mg), boronic acid (1.5 eq.), $K_2CO_3$ (2 eq.) and $Pd(PPh_3)_4$ (0.1 eq.) were dissolved in toluene (2 ml) and heated to 100° C. for 3 to 6 hours. Then, the reaction mixture was diluted with water and extracted with chloroform. Organic layer was washed with saturated $NH_4Cl$, then with water and was dried over $MgSO_4$. After evaporation of solvent, the crude product was purified by column chromatography ($SiO_2$, ethyl acetate in petroleum ether 0-60%).

General Procedure B (Stille Coupling)

Protected nucleoside 8 or 13 (200 mg), tributylstannane (1.2 eq.) and $PdCl_2(PPh_3)_2$ (0.1 eq.) were dissolved in anhydrous DMF (2 ml) and heated to 100° C. for 1 to 3 hours. The volatiles were removed in vacuo and the reaction mixture was purified by column chromatography ($SiO_2$, ethyl acetate in petroleum ether 0-60%).

General Procedure C (Zemplén Deprotection of Benzoylated Nucleosides)

Protected nucleoside (150 mg) was dissolved in methanol (10 ml) and 1M solution of MeONa in MeOH (0.3 eq.) was added. Reaction mixture was stirred at r.t. for 3 to 16 hours. Solvent was evaporated under reduced pressure and crude products were purified by column chromatography (MeOH in dichloromethane, 0-15%).

Example 1

4,6-Dichloro-5-(furan-2-yl)pyrimidine (5)

Solution of 4,6-dichloropyrimidine (3.2 mg, 0.021 mol) in dry THF (35 ml) and added dropwise into an ice-cooled solution of $(TMP)_2Zn\cdot MgCl_2\cdot LiCl$ (0.35 M in THF/toluene 9:1, 30 ml, 10.6 mmol). Reaction mixture was stirred at 0° C. for 1 h, then let warm to r.t. for one hour and added to a pre-stirred mixture of 2-iodofuran (4.44 g, 0.023 mol) and $Pd(PPh_3)_4$ (2.61 g, 2.25 mmol) in dry THF (10 ml). Next reaction mixture was stirred at 65° C. for 16 h. After that, solvent was evaporated under reduced pressure and crude mixture was purified using column chromatography (ethyl acetate in petroleum ether 0-1%) to give compound 5 (2.1 mg, 46%) as a yellowish powder. m.p. 257-265° C. (decomposition). $^1H$ NMR (401 MHz, DMSO) δ 6.73 (dd, 1H, $J_{4,3}$=3.4, $J_{4,5}$=1.8 Hz, H-4-furyl); 6.93 (dd, 1H, $J_{3,4}$=3.4, $J_{3,5}$=0.7 Hz, H-3-furyl); 7.97 (dd, 1H, $J_{5,4}$=1.8, $J$=$_{5,3}$=0.7 Hz, H-5-furyl); 8.96 (s, 1H, H-2), $^{13}C$ NMR (101 MHz, DMSO) δ 112.06, 114.90, 124.65, 143.51, 145.48, 158.15, 161.27. HR MS (EI) for $C_8H_4N_2OCl_2$ [M+]: calcd 213.9701; found 213.9703.

Example 2

4-Azido-6-chloro-5-(furan-2-yl)pyrimidine (6)

Compound 5 (860 mg, 4.03 mmol) was dissolved in dry DMF (20 ml); then LiCl (210 mg, 4.03 mmol) and $NaN_3$ (330 mg, 4.03 mmol) were added. The reaction mixture was stirred at r.t. for 12 h, then it was poured into ethyl acetate and washed two times with water and brine. The organic layer was dried over $Na_2SO_4$, filtered and concentrated. The crude product was purified using column chromatography (ethyl acetate in petroleum ether 0-5%) to give compound 16 (576 mg, 65%) as an orange oil. $^1H$ NMR (400 MHz, DMSO) δ 6.90 (dd, 1H, $J_{4,3}$=3.6, $J_{4,5}$=1.8 Hz, H-4-furyl); 7.77 (dd, 1H, $J_{3,4}$=3.6, $J_{3,5}$=0.8 Hz, H-3-furyl); 8.17 (dd, 1H, $J_{5,4}$=1.8, $J_{5,3}$=0.8 Hz, H-5-furyl); 10.12 (s, 1H, H-2). $^{13}C$ NMR (101 MHz, DMSO) δ 112.70 (C-5); 113.20 (C-4-furyl); 118.03 (C-3-furyl); 137.53 (C-5-furyl); 141.43 (C-6); 143.40 (C-2-furyl); 146.70 (C-2); 149.31 (C-4). HR MS (EI) for $C_8H_4N_5OCl$ [M+]: calcd 221.0104; found 221.0106.

Example 3

4-Chloro-8H-furo[2',3':4,5]pyrrolo[2,3-d]pyrimidine (7)

Solution of azide 6 (540 mg, 2.44 mmol) in TFA (35 ml) was stirred at r.t. under irradiation by UV bulb (4W) for 48 h. After that acid was evaporated and the crude material was purified using column chromatography (ethyl acetate in petroleum ether 0-20%) to give compound 7 (198 mg, 42%) as a yellowish powder. m.p.>300° C. $^1H$ NMR (400 MHz, DMSO) δ 7.05 (d, 1H, $J_{7,6}$=2.1 Hz, H-7); 8.11 (d, 1H, $J_{6,7}$=2.1 Hz, H-6); 8.59 (s, 1H, H-2); 12.67 (s, 1H, NH-8). $^{13}C$ NMR (101 MHz, DMSO) δ 100.89 (C-4a); 104.32 (CH-7); 131.69 (C-7a); 145.80 (C-4); 149.77 (CH-6); 150.25 (CH-2); 153.88 (C-8a). HR MS (APCI) for $C_8H_5ON_3Cl$ [M+H]: calcd 194.01157; found 194.01157.

Example 4

4-Chloro-8-(2,3,5-tri-O-benzoyl-β-D-ribofuranosyl)-8H-furo[2',3':4,5]pyrrolo[2,3-d]pyrimidine (8)

To a solution of base 7 (440 mg; 2.3 mmol) in MeCN (60 ml) BSA (565 µl, 2.3 mmol) was added. The reaction mixture was heated at 60° C. for 30 min, then, TMSOTf (1 ml, 5.71 mmol) and 1-O-acetyl-2,3,5-tri-O-benzoyl-β-D-ribofuranose (2.3 g, 4.6 mmol) were added. Reaction mixture was heated to 60° C. for additional 4 hours. After that the mixture was cooled and then extracted with EtOAc. Organic fraction was washed twice with $NaHCO_3$, water, dried over $Na_2SO_4$ and evaporated under reduced pressure. Crude material was purified using column chromatography (ethyl acetate in petroleum ether 0-15%). Desired nucleoside 8 (900 mg, 62%) was obtained as straw foam. $[\alpha]_D$ –53.5 (c 0.258). $^1H$ NMR (500 MHz, $CDCl_3$): 4.68 (dd, 1H, $J_{gem}$=12.0 Hz, $J_{5'a,4'}$=3.4 Hz, H-5'a); 4.82 (dt, 1H, $J_{4',3'}$=4.7 Hz, $J_{4',5'a}$=$J_{4',5'b}$=3.2 Hz, H-4'); 4.85 (dd, 1H, $J_{gem}$=12.0 Hz, $J_{5'b,4'}$=3.0 Hz, H-5'b); 6.11 (dd, 1H, $J_{3',2'}$=5.9 Hz, $J_{3',4'}$=4.6 Hz, H-3'); 6.29 (t, 1H, =$J_{2',3'}$=$J_{2',1'}$=5.8 Hz, H-2'); 6.84 (d, 1H, $J_{7,6}$=2.2 Hz, H-7); 6.92 (d, 1H, $J_{1',2'}$=5.7 Hz, H-1'); 7.36, 7.42 and 7.44 (3×m, 3×2H, H-m-Bz); 7.54 (m, 1H, H-p-Bz); 7.57-7.62 (m, 2H, H-p-Bz); 7.60 (d, 1H, $J_{6,7}$=2.2 Hz, H-6); 7.92, 8.01 and 8.02 (3×m, 3×2H, H-o-Bz); 8.62 (s, 1H, H-2). $^{13}C$ NMR (125.7 MHz, CDCl3): 63.42 (CH2-5'); 71.06 (CH-3'); 72.82 (CH-2'); 79.87 (CH-4'); 85.41 (CH-1'); 100.15 (C-7); 106.30 (C-4a); 128.35 (C-i-Bz); 128.50, 128.56 and 128.57 (CH-m-Bz); 128.63 and 129.26 (C-i-Bz); 129.66 and 129.82 (CH-o-Bz); 129.96 (C-7a); 133.49 and 133.79 (CH-p-Bz); 136.77 (C-4b); 147.67 (C-4); 148.57 (CH-6); 149.99 (CH-2); 153.79 (C-8a); 165.11, 165.56 and 166.08 (CO). HR MS (ESI) for $C_{34}H_{24}O_8N_3ClNa$ [M+Na]: calcd 660.11441; found 660.11482.

Example 5

4-Methyl-8-(β-D-ribofuranosyl)-8H-furo[2',3':4,5]pyrrolo[2,3-d]pyrimidine (1a)

$(Me)_3Al$ (785 µl, 2M in toluene) and $Pd(PPh_3)_4$ (213 mg, 0.2 mmol) were added to the solution of nucleoside 8 (590 mg, 0.96 mmol) in THF (15 ml); then the reaction mixture was stirred at 70° C. overnight. Solvent was evaporated and crude reaction mixture was purified by chromatographic column (MeOH in DCM 0-15%). Benzoylated nucleoside 9a was directly deprotected using the general procedure C. Nucleoside 1a (149 mg, 50%) was obtained as yellowish crystals, m.p. 195-203° C. (decomposition). $[\alpha]_D$ –39.6 (c 0.252). $^1$H NMR (500 MHz, DMSO-$d_6$): 2.81 (s, 3H, CH$_3$-4); 3.58 (ddd, 1H, $J_{gem}$=11.8 Hz, $J_{5'a,OH}$=5.2 Hz, $J_{5'a,4'}$=4.0 Hz, H-5'a); 3.62 (ddd, 1H, $J_{gem}$=11.8 Hz, $J_{5'b,OH}$=5.5 Hz, $J_{5'b,4'}$=4.1 Hz, H-5'b); 3.94 (td, 1H, $J_{4',5'a}$=$J_{4',5'b}$=4.1 Hz, $J_{4',3'}$=2.4 Hz, H-4'); 4.12 (td, 1H, $J_{3',2'}$=$J_{3',OH}$=4.9 Hz, $J_{3',4'}$=2.4 Hz, H-3'); 4.50 (td, 1H, $J_{2',1'}$=$J_{2',OH}$=7.0 Hz, $J_{2',3'}$=5.3 Hz, H-2'); 5.05 (t, 1H, $J_{OH,5'a}$=$J_{OH,5'b}$=5.3 Hz, OH-5'); 5.21 (d, 1H, $J_{OH,3'}$=4.5 Hz, OH-3'); 5.32 (d, 1H, $J_{OH,2'}$=6.7 Hz, OH-2'); 6.37 (d, 1H, $J_{1',2'}$=7.4 Hz, H-1'); 7.21 (d, 1H, $J_{7,6}$=2.1 Hz, H-7); 8.04 (d, 1H, $J_{6,7}$=2.1 Hz, H-6); 8.68 (s, 1H, H-2). $^{13}$C NMR (125.7 MHz, DMSO-$d_6$): 22.60 (CH$_3$-4); 61.96 (CH$_2$-5'); 70.76 (CH-3'); 72.55 (CH-2'); 85.45 (CH-4'); 85.68 (CH-1'); 101.86 (CH-7); 105.47 (C-4a); 129.08 (C-7a); 137.57 (C-4b); 148.57 (CH-6); 150.48 (CH-2); 153.04 (C-8a); 154.46 (C-4). HR MS (ESI) for C$_{14}$H$_{15}$O$_5$N$_3$Na [M+Na]: calcd 328.09039; found 328.09044.

Example 6

4-Methoxy-8-(β-D-ribofuranosyl)-8H-furo[2',3':4,5] pyrrolo[2,3-d]pyrimidine (1b)

To a suspension of nucleoside 8 (370 mg, 0.58 mmol) in MeOH (25 ml) sodium methoxide (63 mg, 1.16 mmol) was added. The reaction mixture was stirred overnight at r.t., then methanol was evaporated and crude material was purified by column chromatography (MeOH in DCM 0-5%). Nucleoside 1b (144 mg, 77%) was obtained as a yellowish powder, m.p. 216-219° C. $[\alpha]_D$ –40.1 (c 0.172). $^1$H NMR (500 MHz, DMSO-$d_6$): 3.58 (bdt, 1H, $J_{gem}$=11.8 Hz, $J_{5'a,4'}$=$J_{5'a,OH}$=4.5 Hz, H-5'a); 3.61 (bdt, 1H, $J_{gem}$=11.8 Hz, $J_{5'b,4'}$=$J_{5'b,OH}$=4.6 Hz, H-5'b); 3.93 (td, 1H, $J_{4',5'a}$=$J_{4',5'b}$=4.0 Hz, $J_{4',3'}$=2.4 Hz, H-4'); 4.11 (m, 1H, H-3'); 4.12 (s, 3H, CH$_3$O); 4.49 (td, 1H, $J_{2',1'}$=$J_{2',OH}$=7.0 Hz, $J_{2',3'}$=5.3 Hz, H-2'); 5.05 (t, 1H, $J_{OH,5'a}$=$J_{OH,5'b}$=5.3 Hz, OH-5'); 5.21 (d, 1H, $J_{OH,3'}$=4.5 Hz, OH-3'); 5.32 (d, 1H, $J_{OH,2'}$=6.7 Hz, OH-2'); 6.34 (d, 1H, $J_{1',2'}$=7.4 Hz, H-1'); 7.16 (d, 1H, $J_{7,6}$=2.1 Hz, H-7); 7.95 (d, 1H, $J_{6,7}$=2.1 Hz, H-6); 8.45 (s, 1H, H-2). $^{13}$C NMR (125.7 MHz, DMSO-$d_6$): 54.13 (CH$_3$O); 61.99 (CH$_2$-5'); 70.80 (CH-3'); 72.63 (CH-2'); 85.50 (CH-4'); 86.01 (CH-1'); 92.90 (C-4a); 101.78 (CH-7); 127.57 (C-7a); 136.80 (C-4b); 147.81 (CH-6); 150.09 (CH-2); 154.27 (C-8a); 159.92 (C-4). HR MS (ESI) for C$_{14}$H$_{15}$O$_6$N$_3$Na [M+Na]: calcd 344.08531; found 344.08529.

Example 7

4-Methylsulfanyl-8-(β-D-ribofuranosyl)-8H-furo[3',2':4,5]pyrrolo[2,3-d]pyrimidine (1c)

Nucleoside 8 (200 mg, 0.31 mmol) was dissolved in MeOH (12 ml) and sodium thiomethoxide (45 mg, 0.64 mmol) was added in one portion. The reaction mixture was stirred overnight at r.t., after that solvent was evaporated and crude reaction mixture was purified by column chromatography (SiO$_2$, MeOH in DCM 0-5%). Nucleoside 1c (52 mg, 50%) was obtained as a yellowish powder; m.p. 213-217° C. $[\alpha]_D$ –35.5 (c 0.135). $^1$H NMR (500 MHz, DMSO-$d_6$): 2.73 (s, 3H, CH$_3$S); 3.58 (ddd, 1H, $J_{gem}$=11.8 Hz, $J_{5'a,OH}$=5.2 Hz, $J_{5'a,4'}$=4.0 Hz, H-5'a); 3.61 (ddd, 1H, $J_{gem}$=11.8 Hz, $J_{5'b,OH}$=5.4 Hz, $J_{5'b,4'}$=4.0 Hz, H-5'b); 3.93 (td, 1H, $J_{4',5'a}$=$J_{4',5'b}$=4.0 Hz, $J_{4',3'}$=2.4 Hz, H-4'); 4.12 (btd, 1H, $J_{3',2'}$=$J_{3',OH}$=4.9 Hz, $J_{3',4'}$=2.4 Hz, H-3'); 4.49 (btd, 1H, $J_{2',1'}$=$J_{2',OH}$=7.0 Hz, $J_{2',3'}$=5.2 Hz, H-2'); 5.05 (t, 1H, $J_{OH,5'a}$=$J_{OH,5'b}$=5.3 Hz, OH-5'); 5.22 (d, 1H, $J_{OH,3'}$=4.5 Hz, OH-3'); 5.33 (d, 1H, $J_{OH,2'}$=6.6 Hz, OH-2'); 6.34 (d, 1H, $J_{1',2'}$=7.3 Hz, H-1'); 7.20 (d, 1H, $J_{7,6}$=2.1 Hz, H-7); 8.05 (d, 1H, $J_{6,7}$=2.1 Hz, H-6); 8.65 (s, 1H, H-2). $^{13}$C NMR (125.7 MHz, DMSO-$d_6$): 11.63 (CH$_3$S); 61.92 (CH$_2$-5'); 70.74 (CH-3'); 72.61 (CH-2'); 85.53 (CH-4'); 85.80 (CH-1'); 101.83 (CH-7); 103.19 (C-4a); 128.62 (C-7a); 136.92 (C-4b); 148.89 (CH-6); 150.02 (CH-2); 151.08 (C-8a); 156.42 (C-4). ESI MS m/z (rel %): 376 (100) [M+Na]. HR MS (ESI) for C$_{14}$H$_{16}$O$_5$N$_3$S [M+H]: calcd 338.08052; found 338.08061.

Example 8

8-(β-D-ribofuranosyl)-8H-furo[2',3':4,5]pyrrolo[2,3-d]pyrimidin-4-amine (1d)

To a solution of nucleoside 8 (243 mg, 0.38 mmol) in a dry 1.4-dioxane (5 ml) 30% aq. ammonia (15 ml) was added. The reaction mixture was heated in pressure tube at 100° C. for 24 hr. After that solvents were evaporated and crude material was purified by column chromatography (MeOH in DCM 0-5%). Nucleoside 1d (75 mg, 64%) was obtained as a yellowish powder. m.p. 246-253° C. $[\alpha]_D$ –40.8 (c 0.147). $^1$H NMR (500 MHz, DMSO-$d_6$): 3.55 (ddd, 1H, $J_{gem}$=11.8 Hz, $J_{5'a,OH}$=5.5 Hz, $J_{5'a,4'}$=4.1 Hz, H-5'a); 3.60 (ddd, 1H, $J_{gem}$=11.8 Hz, $J_{5'b,OH}$=5.4 Hz, $J_{5'b,4'}$=4.1 Hz, H-5'b); 3.89 (td, 1H, $J_{4',5'a}$=$J_{4',5'b}$=4.1 Hz, $J_{4',3'}$=2.5 Hz, H-4'); 4.09 (td, 1H, $J_{3',2'}$=$J_{3',OH}$=4.9 Hz, $J_{3',4'}$=2.5 Hz, H-3'); 4.48 (td, 1H, $J_{2',1'}$=$J_{2',OH}$=7.0 Hz, $J_{2',3'}$=5.3 Hz, H-2'); 5.08 (t, 1H, $J_{OH,5'a}$=$J_{OH,5'b}$=5.4 Hz, OH-5'); 5.15 (d, 1H, $J_{OH,3'}$=4.6 Hz, OH-3'); 5.25 (d, 1H, $J_{OH,2'}$=6.8 Hz, OH-2'); 6.23 (d, 1H, $J_{1',2'}$=7.3 Hz, H-1'); 7.05 (d, 1H, $J_{7,6}$=2.1 Hz, H-7); 7.06 (bs, 2H, NH$_2$); 7.86 (d, 1H, $J_{6,7}$=2.1 Hz, H-6); 8.09 (s, 1H, H-2). $^{13}$C NMR (125.7 MHz, DMSO-$d_6$): 62.08 (CH$_2$-5'); 70.79 (CH-3'); 72.43 (CH-2'); 85.16 (CH-4'); 85.88 (CH-1'); 90.71 (C-4a); 101.51 (CH-7); 127.25 (C-7a); 138.20 (C-4b); 146.08 (CH-6); 151.41 (CH-2); 153.19 (C-8a); 154.64 (C-4). HR MS (ESI) for C$_{13}$H$_{15}$O$_5$N$_4$ [M+H]: calcd 307.10370; found 307.10374.

Example 9

4-(Furan-2-yl)-8-(2,3,5-tri-O-benzoyl-β-D-ribofuranosyl)-8H-furo[2',3':4,5]pyrrolo[2,3-d]pyrimidine (9e)

Nucleoside 9e was prepared according to the general procedure B. Protected nucleoside 8 (800 mg, 1,256 mmol) and 2-(tributylstannyl)furan (475 μL, 1.5 mmol) were used. Desired product 9e (684 mg, 81%) was obtained as a yellow oil. $^1$H NMR (400 MHz, DMSO-$d_6$) δ 4.67-4.84 (m, 2H); 4.93 (dd, 1H); 6.16 (dd, 1H); 6.40 (dd, 1H); 6.86 (dd, 1H); 6.94 (d, 1H); 7.30 (d, 1H); 7.38-7.54 (m, 6H); 7.58-7.72 (m, 4H); 7.80-7.85 (m, 2H); 7.93-7.99 (m, 2H); 7.99-8.03 (m, H); 8.13-8.17 (m, 2H); 8.75 (s, 1H). HR MS (ESI) for C$_{38}$H$_{28}$O$_9$N$_3$ [M+H]: calcd 670.18201; found 670.18215.

Example 10

4-(Furan-2-yl)-8-(β-D-ribofuranosyl)-8H-furo[2',3':4,5]pyrrolo[2,3-d]pyrimidine (1e)

Compound 9e (630 mg, 0.94 mmol) was deprotected according to the general procedure C. Nucleoside 1e (263 mg, 77%) was obtained as a yellowish powder. m.p. 128-151° C. (decomposition). [α]$_D$ –24.1 (c 0.345). $^1$H NMR (500 MHz, DMSO-d$_6$): 3.61 (ddd, 1H, J$_{gem}$=11.8 Hz, J$_{5'a,OH}$=5.2 Hz, J$_{5'a,4'}$=4.0 Hz, H-5'a); 3.64 (ddd, 1H, J$_{gem}$=11.8 Hz, J$_{5'b,OH}$=5.3 Hz, J$_{5'b,4}$=4.0 Hz, H-5'b); 3.96 (td, 1H, J$_{4',5'a}$=J$_{4',5'b}$=4.0 Hz, J$_{4',3'}$=2.4 Hz, H-4'); 4.14 (btd, 1H, J$_{3',2'}$=J$_{3',OH}$=4.9 HZ, J$_{3',4'}$=2.4 Hz, H-3'); 4.54 (btd, 1H, J$_{2',1'}$=J$_{2',OH}$=7.0 Hz, J$_{2',3'}$=5.3 Hz, H-2'); 5.08 (t, 1H, J$_{OH,5'a}$=J$_{OH,5'b}$=5.3 Hz, OH-5'); 5.23 (d, 1H, J$_{OH,3'}$=4.5 Hz, OH-3'); 5.36 (d, 1H, J$_{OH,2'}$=6.6 Hz, OH-2'); 6.43 (d, 1H, J$_{1',2'}$=7.4 Hz, H-1'); 6.86 (dd, 1H, J$_{4,3}$=3.5 Hz, J$_{4,5}$=1.8 Hz, H-4-furyl); 7.28 (d, 1H, J$_{7,6}$=2.1 Hz, H-7); 7.62 (dd, 1H, J$_{3,4}$=3.5 Hz, J$_{3,5}$=0.9 Hz, H-3-furyl); 8.13 (d, 1H, J$_{6,7}$=2.1 Hz, H-6); 8.14 (bd, 1H, J$_{5,4}$=1.8 Hz, H-5-furyl); 8.78 (s, 1H, H-2). $^{13}$C NMR (125.7 MHz, DMSO-d$_6$): 61.93 (CH$_2$-5'); 70.75 (CH-3'); 72.50 (CH-2'); 85.54 (CH-4'); 85.69 (CH-1'); 99.90 (C-4a); 101.91 (CH-7); 113.17 (CH-4-furyl); 113.21 (CH-3-furyl); 130.59 (C-7a); 137.01 (C-4b); 142.61 (C-4); 146.57 (CH-5-furyl); 148.95 (CH-6); 150.37 (CH-2); 151.65 (C-2-furyl); 154.40 (C-8a). HR MS (ESI) for C$_{17}$H$_{16}$O$_6$N$_3$ [M+H]: calcd 358.10336; found 358.10348.

Example 11

4-(Furan-3-yl)-8-(2,3,5-tri-O-benzoyl-β-D-ribofuranosyl)-8H-furo[2',3':4,5]pyrrolo[2,3-d]pyrimidine (9f)

Nucleoside 9f was prepared according to the general procedure A. Protected nucleoside 8 (210 mg, 0.315 mmol) and furan-3-boronic acid (53 mg, 0.473 mmol) were used. Desired product 9f (193 mg, 92%) was obtained as yellowish oil. $^1$H NMR (400 MHz, CDCl$_3$) δ 4.70 (dd, 1H; 4.81-4.89 (m, 2H); 6.12 (dd, 1H); 6.29 (t, 1H.); 6.89 (d, 1H); 7.03 (d, 1H); 7.34-7.46 (m, 7H); 7.51-7.64 (m, 6H); 7.91 (d, 1H); 7.93 (d, 1H); 8.01-8.06 (s, 4H); 8.88 (s, 1H). HR MS (ESI) for C$_{38}$H$_{28}$O$_9$N$_3$ [M+H]: calcd 670.18201; found 670.18215.

Example 12

4-(Furan-3-yl)-8-(β-D-ribofuranosyl)-8H-furo[2',3':4,5]pyrrolo[2,3-d]pyrimidine (1f)

Compound 9f (170 mg, 0.25 mmol) was deprotected according to the general procedure C. Nucleoside 1f (74 mg, 81%) was obtained as yellowish powder. m.p. 216-220° C. [α]$_D$–23.7 (c 0.135). $^1$H NMR (500 MHz, DMSO-d$_6$): 3.60 (ddd, 1H, J$_{gem}$=11.8 Hz, J$_{5'a,OH}$=5.2 Hz, J$_{5'a,4'}$=4.0 Hz, H-5'a); 3.63 (ddd, 1H, J$_{gem}$=11.8 Hz, J$_{5'b,OH}$=5.4 Hz, J$_{5'b,4'}$=4.0 Hz, H-5'b); 3.96 (td, 1H, J$_{4',5'a}$=J$_{4',5'b}$=4.0 Hz, J$_{4',3'}$=2.4 Hz, H-4'); 4.14 (btd, 1H, J$_{3',2'}$=J$_{3',OH}$=4.9 Hz, J$_{3',4'}$=2.4 Hz, H-3'); 4.54 (td, 1H, J$_{2',1'}$=J$_{2',OH}$=7.0 Hz, J$_{2',3'}$=5.2 Hz, H-2'); 5.08 (t, 1H, J$_{OH,5'a}$=J$_{OH,5'b}$=5.3 Hz, OH-5'); 5.23 (d, 1H, J$_{OH,3'}$=4.5 Hz, OH-3'); 5.35 (d, 1H, J$_{OH,2'}$=6.7 Hz, OH-2'); 6.43 (d, 1H, J$_{1',2'}$=7.4 Hz, H-1'); 7.30 (d, 1H, J$_{7,6}$=2.1 Hz, H-7); 7.43 (dd, 1H, J$_{4,5}$=1.9 Hz, J$_{4,2}$=0.8 Hz, H-4-furyl); 7.98 (t, 1H, J$_{5,2}$=J$_{5,4}$=1.7 Hz, H-5-furyl); 8.15 (d, 1H, J$_{6,7}$=2.1 Hz, H-6); 8.78 (dd, 1H, J$_{2,5}$=1.6 Hz, J$_{2,4}$=0.8 Hz, H-2-furyl); 8.80 (s. 1H. H-2). $^{13}$C NMR (125.7 MHz. DMSO-d$_6$): 66.22 (CH$_2$-5'); 71.04 (CH-3'); 72.83 (CH-2'); 85.83 (CH-4'); 86.00 (CH-1'); 102.35 (CH-7); 109.28 (CH-4-furyl); 125.67 (C-3-furyl); 130.26 (C-7a); 137.06 (C-4b); 144.72 (CH-2-furyl); 145.63 (CH-5-furyl); 146.38 (C-4); 149.23 (CH-6); 150.82 (CH-2); 154.46 (C-8a). HR MS (ESI) for C$_{17}$H$_{16}$O$_6$N$_3$ [M+H]: calcd 358.10336; found 358.10332.

Example 13

4-(Benzofuran-2-yl)-8-(2,3,5-tri-O-benzoyl-β-D-ribofuranosyl)-8H-furo[2',3':4,5]pyrrolo[2,3-d]pyrimidine (9g)

Nucleoside 9g was prepared according to the general procedure A. Protected nucleoside 8 (360 mg, 0.56 mmol) and benzofuran-2-boronic acid (136 mg, 0.84 mmol) were used. Desired product 9g (330 mg, 81%) was obtained as yellow oil. $^1$H NMR (401 MHz, DMSO-d6): 4.56-4.68 (m, 1H); 4.77-4.84 (m, 2H); 6.18-6.46 (m, 2H); 6.98 (d, 1H.); 7.34-7.54 (m, 8H); 7.59-7.70 (m, 3H); 7.72-8.01 (m, 10H); 8.24 (d, 1H); 8.90 (s, 1H). HR MS (ESI) for C$_{42}$H$_{30}$O$_9$N$_3$ [M+H]: calcd 720.19766; found 720.19781.

Example 14

4-(Benzofuran-2-yl)-8-(β-D-ribofuranosyl)-8H-furo[2',3':4,5]pyrrolo[2,3-d]pyrimidine (1g)

Compound 9g (260 mg, 0.36 mmol) was deprotected according to the general procedure C. Nucleoside 1g (101 mg, 69%) was obtained as a lemon powder, m.p. 223-240° C. (decomposition). [α]$_D$–21.6 (c 0.241). $^1$H NMR (500 MHz, DMSO-d$_6$): 3.59-3.68 (m, 2H, H-5'); 3.98 (td, 1H, J$_{4',5'a}$=J$_{4',5'b}$=4.0 Hz, J$_{4',3}$=2.4 Hz, H-4'); 4.17 (bddd, 1H, J$_{3',2'}$=5.2 Hz, J$_{3',OH}$=4.3 Hz, J$_{3',4}$=2.4 Hz, H-3'); 4.56 (td, 1H, J$_{2',1'}$=J$_{2',OH}$=7.0 Hz, J$_{2',3'}$=5.2 Hz, H-2'); 5.12 (t, 1H, J$_{OH,5'a}$=J$_{OH,5'b}$=5.3 Hz, OH-5'); 5.27 (d, 1H, J$_{OH,3'}$=4.3 Hz, OH-3'); 5.39 (d, 1H, J$_{OH,2'}$=6.6 Hz, OH-2'); 6.47 (d, 1H, J$_{1',2'}$=7.4 Hz, H-1'); 7.34 (d, 1H, J$_{7,6}$=2.1 Hz, H-7); 7.39 (ddd, 1H, J$_{5,4}$=7.8 Hz, J$_{5,6}$=7.2 Hz, J$_{5,7}$=1.0 Hz, H-5-benzofuryl); 7.50 (ddd, 1H, J$_{6,7}$=8.3 Hz, J$_{6,5}$=7.2 Hz, J$_{6,4}$=1.3 Hz, H-6-benzofuryl); 7.79 (dq, 1H, J$_{7,6}$=8.3 Hz, J$_{7,5}$=J$_{7,4}$=J$_{7,3}$=0.9 Hz, H-7-benzofuryl); 7.89 (ddd, 1H, J$_{4,5}$=7.8 Hz, J$_{4,6}$=1.3 Hz, J$_{4,7}$=0.7 Hz, H-4-benzofuryl); 8.08 (d, 1H, J$_{3,7}$=1.0 Hz, H-3-benzofuryl); 8.23 (d, 1H, J$_{6,7}$=2.1 Hz, H-6); 8.89 (s, 1H, H-2). $^{13}$C NMR (125.7 MHz, DMSO-d$_6$): 61.91 (CH$_2$-5'); 70.76 (CH-3'); 72.58 (CH-2'); 85.63 (CH-4'); 85.79 (CH-1'); 101.12 (C-4a); 102.04 (CH-7); 108.81 (CH-3-benzofuryl); 111.91 (CH-7-benzofuryl); 122.70 (CH-4-benzofuryl); 124.02 (CH-5-benzofuryl); 126.83 (CH-6-benzofuryl); 128.22 (C-3a-benzofuryl); 131.34 (C-7a); 136.85 (C-4b); 142.32 (C-4); 149.57 (CH-6); 150.33 (CH-2); 153.19 (C-2-benzofuryl); 154.60 (C-8a); 155.36 (C-7a-benzofuryl). HR MS (ESI) for C$_{21}$H$_{18}$O$_6$N$_3$ [M+H]: calcd 408.11901; found 408.11911.

Example 15

N,N-Dimethyl-8-(2,3,5-tri-O-benzoyl-β-D-ribofuranosyl)-8H-furo[2',3':4,5]pyrrolo[2,3-d]pyrimidin-4-amine (9h)

To the solution of nucleoside 8 (460 mg, 0.72 mmol) in isopropanol (20 ml) dimethylamine (460 μl, 2M in THF) was added in one portion. Reaction mixture was stirred at r.t. overnight. Solvent was evaporated and then the crude mixture was purified by column chromatography (ethyl acetate in petroleum ether 0-35%). Desired nucleoside 9h (280 mg, 61%) was obtained as yellow oil. $^1$H NMR (401 MHz, DMSO-d6) δ 3.39 (s, 6H); 4.64-4.80 (m, 2H); 4.86 (dd, 1H); 6.11 (dd, 1H); 6.32 (dd, 1H); 6.83 (d, 1H); 7.10 (d, 1H);

7.38-7.46 (m, 2H); 7.48-7.55 (m, 4H); 7.59-7.66 (m, 1H); 7.67-7.73 (m, 2H); 7.80-7.83 (m, 3H); 7.96-7.99 (m, 4H); 8.17 (s, 1H). HR MS (ESI) for $C_{36}H_{31}O_8N_4$ [M+H]: calcd 647.21364; found 647.21374.

Example 16

N,N-dimethyl-8-(β-D-ribofuranosyl)-8H-furo[2',3':4,5]pyrrolo[2,3-d]pyrimidin-4-amine (1h)

Derivative 9h (250 mg, 0.39 mmol) was deprotected using the general procedure C. Compound 1h (129 mg, 67%) was obtained as yellow crystals, m.p. 212-255° C. (decomposition). $[α]_D$–40.0 (c 0.065). $^1$H NMR (500 MHz, DMSO-$d_6$): 3.40 (s, 6H, $(CH_3)_2N$); 3.56 (dd, 1H, $J_{gem}$=11.8 Hz, $J_{5'a,4'}$=4.1 Hz, H-5'a); 3.60 (dd, 1H, $J_{gem}$=11.8 Hz, $J_{5'b,4'}$=4.1 Hz, H-5'b); 3.89 (td, 1H, $J_{4',5'a}$=$J_{4'5'b}$=4.1 Hz, $J_{4',3'}$=2.7 Hz, H-4'); 4.10 (dd, 1H, $J_{3',2'}$=5.4 Hz, $J_{3',4'}$=2.7 Hz, H-3'); 4.46 (dd, 1H, $J_{2',1'}$=7.3 Hz, $J_{2',3'}$=5.4 Hz, H-2'); 4.97-5.69 (m, 3H, OH-2',3',5'); 6.29 (d, 1H, $J_{1',2'}$=7.3 Hz, H-1'); 7.08 (d, 1H, $J_{7,6}$=2.1 Hz, H-7); 7.82 (d, 1H, $J_{6,7}$=2.1 Hz, H-6); 8.16 (s, 1H, H-2). $^{13}$C NMR (125.7 MHz, DMSO-$d_6$): 38.14 (($CH_3)_2N$); 62.04 ($CH_2$-5'); 70.72 (CH-3'); 72.42 (CH-2'); 85.15 (CH-4'); 85.94 (CH-1'); 90.78 (C-4a); 101.71 (CH-7); 124.75 (C-7a); 138.01 (C-4b); 145.87 (CH-6); 150.43 (CH-2); 153.31 (C-8a); 155.01 (C-4). HR MS (ESI) for $C_{15}H_{19}O_5N_4$ [M+H]: calcd 335.13500; found 335.13512.

Example 17

4,6-Dichloro-5-(1-methyl-1H-pyrrol-2-yl)pyrimidine (10)

Solution of 4,6-dichloropyrimidine (3) (5.52 g, 37 mmol) in dry THF (15 ml) was added dropwise to $TMP_2Zn \cdot 2MgCl_2 \cdot 2LiCl$ (0.35 M in THF/toluene 9:1, 59.5 ml, 21 mmol) at 0° C. and reaction mixture was stirred at this temperature for 1 h, then it was warmed to r.t. and stirred for another 1 h. Resulting solution was added to a mixture of 2-iodo-1-methylpyrrole (7.66 g, 37 mmol) and $Pd(PPh_3)_4$ (4.3 g, 3.7 mmol) in dry THF (20 ml) and stirred at 65° C. for 16 h. Then, solvent was evaporated under reduced pressure, and crude mixture was purified by flash chromatography on silica gel (0 to 5% of ethyl acetate in petroleum ether) to give 10 as a yellowish solid (6.4 g, 28 mmol, 75%; m.p. 56-58° C.). $^1$H NMR (400.0 MHz, DMSO-$d_6$): 3.43 (s, 3H); 6.15 (dd, 1H); 6.18 (dd, 1H); 6.97 (dd, 1H); 8.96 (s, 1H). HR MS (EI) for $C_9H_7Cl_2N_3$: calcd 227.0017; found 227.0019.

Example 18

4-Azido-6-chloro-5-(1-methyl-1H-pyrrol-2-yl)pyrimidine (11)

Compound 10 (1 g, 4.4 mmol); $NaN_3$ (285 mg, 4.4 mmol) and LiCl (186 mg, 4.4 mmol) were dissolved in dry DMF (10 ml) and resulting solution was stirred at r.t. for 16 h. After that, reaction mixture was extracted with ethyl acetate, and combined organic layers were dried over anhydrous $MgSO_4$ and concentrated under reduced pressure. Crude material was purified by flash chromatography on silica gel (0 to 10% of ethyl acetate in petroleum ether) furnishing 11 as a yellow oil (1.01 g, 4.3 mmol, 98%). $^1$H NMR (400.0 MHz, $CDCl_3$): 3.46 (s, 3H); 6.21 (dd, 1H); 6.28 (dd, 1H); 6.81 (dd, 1H); 8.69 (s, 1H). HR MS (EI) for $C_9H_7ClN_6$: calcd 234.0421; found 234.0420.

Example 19

4-Chloro-5-methyl-5,8-dihydropyrrolo[2',3':4,5]pyrrolo[2,3-d]pyrimidine (12)

Mixture of azide 11 (350 mg, 1.5 mmol) and 1.4-dibromobenzene (3.54 g, 15 mmol) was heated at 180° C. for 30 min with argon inlet and gas outlet. Crude reaction mixture was purified by flash chromatography on silica gel (25 to 40% of ethyl acetate in petroleum ether) furnishing 12 as a white solid (280 mg, 1.35 mmol, 90%; m.p. 231-236° C.). $^1$H NMR (400.0 MHz, DMSO-$d_6$): 4.07 (s, 3H); 6.17 (d, 1H); 7.18 (d, 1H); 8.45 (s, 1H); 12.18 (bs, 1H). HR MS (EI) for $C_9H_7ClN_4$: calcd 206.0359; found 206.0357.

Example 20

4-Chloro-5-methyl-8-(2,3,5-tri-O-benzoyl-β-D-ribofuranosyl)-5,8-dihydropyrrolo[2',3':4,5]pyrrolo[2,3-d]pyrimidine (13)

BSA (0.59 ml, 2.4 mmol) was added to a suspension of 12 (496 mg, 2.4 mmol) in dry acetonitrile (20 ml); and resulting mixture was stirred at r.t. for 30 min. Subsequently, 1-O-acetyl-2.3.5-tri-O-benzoyl-β-D-ribofuranose (1.82 g, 3.6 mmol) and TMSOTf (0.43 ml, 2.4 mmol) were added, and reaction mixture was stirred at 80° C. for 3 h. After cooling to r.t., resulting solution was extracted with ethyl acetate. Combined organic layers were dried over anhydrous $MgSO_4$ and concentrated under reduced pressure. Crude material was purified by flash chromatography on silica gel (5 to 50% of ethyl acetate in petroleum ether) to give desired benzoylated nucleoside 13 as a yellow foam (1.19 g, 1.82 mmol, 76%). $^1$H NMR (400.0 MHz, DMSO-$d_6$): 4.08 (s, 3H); 4.67 (dd, 1H); 4.78 (dd, 1H); 4.90 (td, 1H); 6.12 (dd, 1H); 6.37 (t, 1H); 6.47 (d, 1H); 6.89 (d, 1H); 7.21 (d, 1H); 7.40 (m, 2H); 7.51 (m, 4H); 7.61 (m, 1H); 7.68 (m, 2H); 7.80 (m, 2H); 7.96 (m, 4H); 8.52 (s, 1H). HR MS (ESI) for $C_{35}H_{28}ClN_4O_7$ [M+H]: calcd 651.16410; found 651.16443.

Example 21

4,5-Dimethyl-8-(β-D-ribofuranosyl)-5,8-dihydropyrrolo[2',3':4,5]pyrrolo[2,3-d]pyrimidine (2a)

Nucleoside 13 (150 mg, 0.23 mmol) and $Pd(PPh_3)_4$ (13 mg, 0.012 mmol) were dissolved in dry THF (6 ml); then, $AlMe_3$ (2 M in toluene; 0.24 ml, 0.46 mmol) was added and resulting mixture was stirred at 70° C. for 3 h. After cooling to r.t., reaction was quenched with methanol and filtered through Celite. Solvents were removed under reduced pressure, and crude material was dissolved in dry methanol (10 ml). Subsequently, sodium methoxide (4.37 M in methanol; 16 μl, 0.07 mmol) was added, and reaction mixture was stirred at r.t. for 3 h. Solvent was evaporated under reduced pressure, and crude mixture was purified by flash chromatography on silica gel (0 to 10% of methanol in dichloromethane) furnishing free nucleoside 2a as a white powder (64 mg, 0.2 mmol, 89%; m.p. 237-241° C.). $^1$H NMR (400.0 MHz, DMSO-$d_6$): 2.91 (s, 3H); 3.57 (m, 2H); 3.89 (td, 1H); 4.07 (s, 3H); 4.11 (m, 1H); 4.58 (td, 1H); 4.97 (t, 1H); 5.14 (d, 1H); 5.18 (d, 1H); 6.33 (d, 1H); 6.35 (d, 1H); 7.08 (d, 1H); 8.54 (s, 1H). HR MS (ESI) for $C_{15}H_{19}N_4O_4$ [M+H]: calcd 319.14008; found 319.14014.

Example 22

4-Methoxy-5-methyl-8-(β-D-ribofuranosyl)-5,8-dihydropyrrolo[2',3':4,5]pyrrolo[2,3-d]pyrimidine (2b)

Sodium methoxide (4.37 M in methanol; 0.1 ml, 0.46 mmol) was added to a suspension of nucleoside 13 (150 mg, 0.23 mmol) in dry methanol (10 ml); and reaction mixture was stirred at r.t. for 12 h. Solvent was evaporated under reduced pressure, and crude mixture was purified by flash chromatography on silica gel (0 to 10% of methanol in dichloromethane) furnishing free nucleoside 2b as a white powder (63 mg, 0.19 mmol, 83%; m.p. 231-234° C.). $^1$H NMR (400.0 MHz, DMSO-$d_6$): 3.57 (m, 2H); 3.88 (td, 1H); 3.98 (s, 3H); 4.10 (m, 1H); 4.12 (s, 3H); 4.58 (td, 1H); 4.97 (t, 1H); 5.14 (d, 1H); 5.20 (d, 1H); 6.30 (d, 1H); 6.32 (d, 1H); 7.02 (d, 1H); 8.36 (s, 1H). HR MS (ESI) for $C_{15}H_{19}N_4O_5$ [M+H]: calcd 335.13500; found 335.13519.

Example 23

5-Methyl-4-(methylsulfanyl)-8-(β-D-ribofuranosyl)-5,8-dihydropyrrolo[2',3':4,5]pyrrolo-[2,3-d]-pyrimidine (2c)

Sodium thiomethoxide (32 mg, 0.46 mmol) was added to a suspension of nucleoside 13 (150 mg, 0.23 mmol) in dry methanol (10 ml); and reaction mixture was stirred at r.t. for 12 h. Solvent was evaporated under reduced pressure, and crude mixture was purified by flash chromatography on silica gel (0 to 10% of methanol in dichloromethane). Free nucleoside 2c was obtained as a white powder (62 mg, 0.18 mmol, 77%; m.p. 212-214° C.). $^1$H NMR (400.0 MHz, DMSO-$d_6$): 2.72 (s, 3H); 3.58 (m, 2H); 3.89 (td, 1H); 4.10 (m, 1H); 4.15 (s, 3H); 4.57 (td, 1H); 4.97 (t, 1H); 5.14 (d, 1H); 5.20 (d, 1H); 6.33 (d, 1H); 6.36 (d, 1H); 7.11 (d, 1H); 8.56 (s, 1H). HR MS (ESI) for $C_{15}H_{19}N_4O_4S$ [M+H]: calcd 351.11215; found 351.11236.

Example 24

5-methyl-8-(β-D-ribofuranosyl)-5,8-dihydropyrrolo[2',3':4,5]pyrrolo[2,3-d]pyrimidin-4-amine (2d)

Nucleoside 13 (150 mg, 0.23 mmol) was dissolved in a mixture of 1,4-dioxane (2 ml) and 30% aq. ammonia (2 ml) in a pressure tube. Reaction mixture was stirred at 120° C. for 12 h, then cooled to r.t. and concentrated under reduced pressure. Purification by flash chromatography on silica gel (0 to 30% of methanol in dichloromethane) afforded free nucleoside 2d as a violet powder (54 mg, 0.17 mmol, 75%; m.p. 240-245° C. (decomposition)). $^1$H NMR (400.0 MHz, DMSO-$d_6$): 3.55 (m, 2H); 3.85 (td, 1H); 4.02 (s, 3H); 4.08 (m, 1H); 4.56 (td, 1H); 5.04 (t, 1H); 5.12 (d, 1H); 5.16 (d, 1H); 6.20 (d, 1H); 6.22 (d, 1H); 6.32 (bs, 2H); 6.88 (d, 1H); 8.08 (s, 1H). HR MS (ESI) for $C_{14}H_{18}N_5O_4$ [M+H]: calcd 320.13533; found 320.13555.

Example 25

4-(Furan-2-yl)-5-methyl-8-(2,3,5-tri-O-benzoyl-β-D-ribofuranosyl)-5,8-dihydropyrrolo[2',3':4,5]pyrrolo[2,3-d]pyrimidine (14e)

Compound 14e was prepared from 13 (185 mg, 0.28 mmol) according to the general procedure B (reaction time: 3 hours). It was obtained as a yellowish foam (184 mg, 0.27 mmol, 95%). $^1$H NMR (400.0 MHz, DMSO-$d_6$): 3.85 (s, 3H); 4.68 (dd, 1H); 4.78 (dd, 1H); 4.89 (ddd, 1H); 6.14 (dd, 1H); 6.41 (t, 1H); 6.46 (d, 1H); 6.80 (dd, 1H); 6.94 (d, 1H); 7.16 (d, 1H); 7.27 (dd, 1H); 7.38-7.42 (m, 2H); 7.48-7.54 (m, 4H); 7.58-7.63 (m, 1H); 7.66-7.70 (m, 2H); 7.80-7.83 (m, 2H); 7.97-8.00 (m, 4H); 8.07 (dd, 1H); 8.65 (s, 1H). HR MS (ESI) for $C_{39}H_{31}N_4O_8$ [M+H]: calcd 683.21364; found 683.21375.

Example 26

4-(Furan-2-yl)-5-methyl-8-(β-D-ribofuranosyl)-5,8-dihydropyrrolo[2',3':4,5]pyrrolo[2,3-d]pyrimidine (2e)

Compound 14e (152 mg, 0.223 mmol) was deprotected using the general procedure C (reaction time: 3 hours). Free nucleoside 2e was obtained as a yellow solid (72 mg, 0.2 mmol, 92%; m.p. 245-253° C.). $^1$H NMR (500.0 MHz, DMSO-$d_6$): 3.58, 3.62 (2×ddd, 2×1H); 3.85 (s, 3H); 3.92 (td, 1H); 4.13 (dt, 1H); 4.62 (ddd, 1H); 5.01 (t, 1H); 5.19 (d, 1H); 5.25 (d, 1H); 6.43 (d, 1H); 6.44 (d, 1H); 6.81 (dd, 1H); 7.17 (d, 1H); 7.26 (dd, 1H); 8.07 (dd, 1H); 8.65 (s, 1H). HR MS (ESI) for $C_{18}H_{19}N_4O_5$ [M+H]: calcd 371.13500; found 371.13503.

Example 27

4-(Furan-3-yl)-5-methyl-8-(2,3,5-tri-O-benzoyl-β-D-ribofuranosyl)-5,8-dihydropyrrolo[2',3':4,5]pyrrolo[2,3-d]pyrimidine (14f)

Nucleoside 14f was prepared from 13 (185 mg, 0.284 mmol) according to the general procedure A (reaction time: 3 hours). It was obtained as a yellowish foam (165 mg, 0.242 mmol, 85%). $^1$H NMR (400.0 MHz, DMSO-$d_6$): 3.50 (s, 3H); 4.68 (dd, 1H); 4.77 (dd, 1H); 4.90 (ddd, 1H); 6.13 (dd, 1H); 6.40-6.43 (m, 2H); 6.93-6.95 (m, 2H); 7.06 (d, 1H); 7.39-7.43 (m, 2H); 7.49-7.55 (m, 4H); 7.59-7.63 (m, 1H); 7.66-7.71 (m, 2H); 7.80-7.83 (m, 2H); 7.87 (dd, 1H); 7.97-8.01 (m, 4H); 8.25 (dd, 1H); 8.68 (s, 1H). HR MS (ESI) for $C_{39}H_{31}N_4O_8$ [M+H]: calcd 683.21364; found 683.21379.

Example 28

4-(Furan-3-yl)-5-methyl-8-(β-D-ribofuranosyl)-5,8dihydropyrrolo[2',3':4,5]pyrrolo[2,3-d]pyrimidine (2f)

Compound 14e (149 mg, 0.218 mmol) was deprotected using the general procedure C (reaction time: 3 hours) to give 2f as yellowish solid (67 mg, 0.181 mmol, 83%; m.p. 202-207° C.). $^1$H NMR (500.0 MHz, DMSO-$d_6$): 3.51 (s, 3H); 3.57, 3.61 (2×bdd, 2×1H); 3.91 (td, 1H); 4.13 (dd, 1H); 4.61 (dd, 1H); 5.00 (bs, 1H); 5.23 (bs, 2H); 6.405 (d, 1H); 6.409 (d, 1H); 6.94 (dd, 1H); 7.08 (d, 1H); 7.89 (t, 1H); 8.25 (dd, 1H); 8.67 (s, 1H). HR MS (ESI) for $C_{18}H_{19}N_4O_5$ [M+H]: calcd 371.13500; found 371.13507.

Example 29

4-(Benzofuran-2-yl)-5-methyl-8-(2,3,5-tri-O-benzoyl-β-D-ribofuranosyl)-5,8-dihydropyrrolo[2',3':4,5]pyrrolo[2,3-d]pyrimidine (14g)

Nucleoside 13 (185 mg, 0.284 mmol) was subjected to a Suzuki coupling reaction according to the general procedure A (reaction time: 3 hours) to furnish 14g as a yellowish foam (179 mg, 0.244 mmol, 86%). $^1$H NMR (400.0 MHz, DMSO-$d_6$): 3.88 (s, 3H); 4.70 (dd, 1H); 4.79 (dd, 1H); 4.91 (ddd, 1H); 6.15 (dd, 1H); 6.43 (t, 1H); 6.51 (d, 1H); 6.97 (d, 1H); 7.21 (d, 1H); 7.35-7.46 (m, 4H); 7.49-7.54 (m, 4H); 7.59-7.63 (m, 1H); 7.66-7.71 (m, 2H); 7.72 (d, 1H); 7.78-7.83 (m, 4H); 7.98-8.01 (m, 4H); 8.74 (s, 1H). HR MS (ESI) for $C_{43}H_{33}N_4O_8$ [M+H]: calcd 733.22929; found 733.22946.

Example 30

4-(Benzofuran-2-yl)-5-methyl-8-(β-D-ribofuranosyl)-5,8-dihydropyrrolo[2',3':4,5]pyrrolo[2,3-d]pyrimidine (2g)

Nucleoside 14g (148 mg, 0.2 mmol) was deprotected according to the general procedure C (reaction time: 3 hours) to give 2g as a yellow solid (74 mg, 0.18 mmol, 90%; m.p. 145-154° C.). $^1$H NMR (500.0 MHz, DMSO-$d_6$): 3.60 (ddd, 1H); 3.64 (ddd, 1H); 3.88 (s, 3H); 3.94 (td, 1H); 4.15 (ddd, 1H); 4.64 (ddd, 1H); 5.01 (t, 1H); 5.19 (d, 1H); 5.27 (d, 1H); 6.46 (d, 1H); 6.49 (d, 1H); 7.22 (d, 1H); 7.38 (ddd, 1H); 7.45 (ddd, 1H); 7.71 (d, 1H); 7.80 (dq, 1H); 7.83 (ddd, 1H); 8.75 (s, 1H). HR MS (ESI) for $C_{22}H_{21}N_4O_5$ [M+H]: calcd 421.15065; found 421.15071.

Example 31

N,N,5-trimethyl-8-(2,3,5-tri-O-benzoyl-β-D-ribofuranosyl)-5,8-dihydropyrrolo[2',3':4,5]pyrrolo[2,3-d]pyrimidin-4-amine (14h)

Protected nucleoside 13 (185 mg, 0.284 mmol) was dissolved in a mixture of isopropanol (10 ml) and THF (4 ml), and dimethylamine (2 M solution in THF; 0.85 ml; 1.7 mmol) was added. After the reaction mixture was stirred at 50° C. for 1 day, solvents were evaporated and crude material was purified by column chromatography on silica gel (20 to 60% of ethyl acetate in petroleum ether) to yield 14h as a white foam (140 mg, 0.212 mmol, 75%). $^1$H NMR (400.0 MHz, DMSO-$d_6$): 3.00 (s, 6H); 3.97 (s, 3H); 4.64 (dd, 1H); 4.74 (dd, 1H); 4.84 (ddd, 1H); 6.11 (dd, 1H); 6.37-6.40 (m, 2H); 6.84 (d, 1H); 6.99 (d, 1H); 7.39-7.43 (m, 2H); 7.47-7.55 (m, 4H); 7.59-7.63 (m, 1H); 7.65-7.71 (m, 2H); 7.80-7.84 (m, 2H); 7.95-8.00 (m, 4H); 8.27 (s, 1H). HR MS (ESI) for $C_{37}H_{34}N_5O_7$ [M+H]: calcd 660.24527; found 660.24537.

Example 32

N,N,5-trimethyl-8-(β-D-ribofuranosyl)-5,8-dihydropyrrolo[2',3':4,5]pyrrolo[2,3-d]pyrimidin-4-amine (2h)

Compound 14h (125 mg, 0.189 mmol) was deprotected using the general procedure C (reaction time: 3 hours) to give free nucleoside 2h as a pale yellow solid (47 mg, 0.135 mmol, 72%; m.p. 99-106° C.). $^1$H NMR (400.0 MHz, DMSO-$d_6$): 3.01 (s, 6H); 3.56 (m, 2H); 3.87 (ddd, 1H); 3.99 (s, 3H); 4.10 (dd, 1H); 4.59 (dd, 1H); 5.00 (bs, 1H); 5.16 (bs, 2H); 6.28 (d, 1H); 6.34 (d, 1H); 7.02 (d, 1H); 8.27 (s, 1H). HR MS (ESI) for $C_{16}H_{22}N_5O_4$ [M+H]: calcd 348.16663; found 348.16670.

Example 33

4-chloro-5-methyl-8-(β-D-ribofuranosyl)-5,8-dihydropyrrolo[2',3':4,5]pyrrolo[2,3-d]pyrimidine (2i)

Protected nucleoside 13 (100 mg, 0.154 mmol) was dissolved in a mixture of 1,4-dioxane (3 ml) and 30% aq. ammonia (3 ml) in a pressure tube. After stirring at 100° C. for 1 h, the mixture was cooled to r.t. and concentrated under reduced pressure. Column chromatography of the crude mixture yielded free nucleoside 2i as a yellowish solid (34 mg, 0.1 mmol, 65%; m.p. 217-219° C.). $^1$H NMR (400.0 MHz, DMSO-$d_6$): 3.56-3.63 (m, 2H); 3.92 (td, 1H); 4.11-4.14 (m, 4H); 4.58 (td, 1H); 4.98 (t, 1H); 5.18 (d, 1H); 5.25 (d, 1H); 6.37 (d, 1H); 6.46 (d, 1H); 7.22 (d, 1H); 8.54 (s, 1H). HR MS (ESI) for $C_{14}H_{15}N_4O_4ClNa$ [M+Na]: calcd 361.06740; found 361.06744.

In Vitro Antitumor Activity

MTT test (Nosková V. et al., Neoplasma 2002, 49, 418-425) was used for in vitro evaluation of antitumor activities of newly synthesized compounds on cell lines derived from normal tissues or tumors. Specifically, cell lines K562 (human acute myeloid leukemia); K562-Tax (human acute myeloid leukemia, paclitaxel resistant subline, overexpress multiple drug resistant protein PgP); CEM (T-lymfoblastic leukemia); CEM-DNR-bulk (T-lymfoblastic leukemia, doxorubicin resistant); A549 (human lung adenocarcinoma); HCT116p53 wt (human colorectal cancer, wild-type); HCT116p53−/− (human colorectal cancer, mutant p53) a U2OS (human bone osteosarcoma) were used. Express characteristics, susceptibility profiles of classic antitumor drugs as well as methodology of cytotoxic MTT test have been repeatedly published (Denizot, F.; Lang, R., *J. Immunol. Meth.* 1986, 89, 271-277; Noskova, V., see above; Šarek J. et al., *J, Med. Chem.*, 2003).

Results of Biological Testing

If tested compounds showed activity in in vitro cytotoxic test (Table 4); it was selective against broad spectrum of cancer cell lines of various histogenetic origin (mesenchymal or epithelial tumors) with significantly lower activity against normal human fibroblasts (MRC-5 cell line). $IC_{50}$ values of compounds 1d-g and 2e-g were in micromolar range, $IC_{50}$ values of compounds 1a-c and 2a-c were sub-micromolar to nanomolar. Cytotoxic activity against cancer cells was independent on p53 gene status, same activities were found for HCT116 (p53 wild type) and for mutant line with deleted gene HCT116 (p53 −/−).

TABLE 4

Cytotoxic activities of prepared compounds

| Compound | A549 | CCRF-CEM | CEM-DNR | HCT116 | HCT116p53 | K562 | K562-TAX | U2OS | MRC-5 |
|---|---|---|---|---|---|---|---|---|---|
| 1a | C | B | E | B | B | B | C | B | E |
| 1b | C | A | C | B | B | B | B | B | D |
| 1c | C | B | C | B | B | B | C | B | C |
| 1d | E | E | E | E | E | C | E | C | E |
| 1e | E | B | E | E | E | C | C | C | E |
| 1f | E | B | E | D | D | B | C | B | E |
| 1g | E | D | E | E | E | E | D | E | E |
| 1h | E | E | E | E | E | E | E | E | E |
| 2a | — | B | E | B | B | B | E | B | E |
| 2b | E | B | E | B | B | B | E | C | E |
| 2c | E | B | E | B | B | B | E | C | E |
| 2d | E | E | E | E | E | E | E | E | E |
| 2e | E | E | E | E | E | E | E | C | E |
| 2f | E | E | E | E | C | C | E | C | E |
| 2g | E | D | E | E | E | E | E | E | E |
| 2h | E | E | E | E | E | E | E | E | E |
| 2i | C | A | E | A | A | A | E | C | E |

$IC_{50}$: A = 10-200 nmol · l$^{-1}$
B = 200-900 nmol · l$^{-1}$
C = 0.9-10 μmol · l$^{-1}$
D = 10-25 μmol · l$^{-1}$
E = 25-50 μmol · l$^{-1}$.

INDUSTRIAL APPLICABILITY

The compounds disclosed in this patent are useful as pharmaceuticals or components of drugs effective against cancers and leukemias.

The invention claimed is:

1. 4-Substituted heteropentadieno-pyrrolopyrimidine ribonucleosides of general formula I:

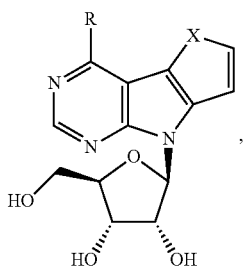

(I)

wherein
R is selected from the group consisting of:
C1-C5 alkyl, optionally substituted by at least one substitutent selected from hydroxy, sulfanyl, amino, C1-C5 alkoxy, C1-C5 sulfanyl, C1-C5 alkylamino, di(C1-C5 alkyl)amino;
C2-C6 alkenyl, optionally substituted by at least one substitutent selected from hydroxy, sulfanyl, amino, C1-C5 alkoxy, C1-C5 sulfanyl, C1-C5 alkylamino, di(C1-C5 alkyl)amino;
C6-C12 aryl, optionally substituted by at least one substitutent selected from C1-C5 alkyl, hydroxy, sulfanyl, amino, C1-C5 alkoxy, C1-C5 sulfanyl, C1-C5 alkylamino, di(C1-C5 alkyl)amino;
C4-12 heteroaryl, comprising at least one O atom; optionally substituted by at least one substitutent selected from C1-C5 alkyl, hydroxy, sulfanyl, amino, C1-C5 alkoxy, C1-C5 sulfanyl, C1-C5 alkylamino, di(C1-C5 alkyl)amino;
amino,
C1-C5 alkylamino,
di(C1-C5 alkyl)amino,
C1-C5 alkoxy,
C1-C5 alkylsulfanyl, and
halogen; and
—X— is selected from —O—, —NH— and N(C1-C5 alkyl)-;
or pharmaceutically acceptable salt thereof, their optical isomers, or mixtures or racemic mixtures of such optical isomers.

2. 4-Substituted heteropentadieno-pyrrolopyrimidine ribonucleosides of general formula I according to claim 1, where R is selected from the group consisting of C1-C5 alkyl, phenyl, naphthyl, 2-furyl, 3-furyl, benzofuryl, dibenzofuryl, C1-C5 alkylsulfanyl, amino, C1-C5 alkylamino, di(C1-C5 alkyl)amino, C1-C5 alkoxy and halogen group.

3. 4-Substituted heteropentadieno-pyrrolopyrimidine ribonucleosides of general formula I according to claim 1, where R is selected from the group consisting of furan-2-yl, furan-3-yl, benzofuran-2-yl, methylsulfanyl, methoxy, amino, dimethylamino, methyl and chloro.

4. 4-Substituted heteropentadieno-pyrrolopyrimidine ribonucleosides of general formula I according to claim 1, being selected from the following compounds:
4-methyl-8-(β-D-ribofuranosyl)-8H-furo[2',3':4,5]pyrrolo[2,3-d]pyrimidine,
4-methoxy-8-(β-D-ribofuranosyl)-8H-furo[2',3':4,5]pyrrolo[2,3-d]pyrimidine,
4-(methylsulfanyl)-8-(β-D-ribofuranosyl)-8H-furo[2',3':4,5]pyrrolo[2,3-d]pyrimidine,
8-(β-D-ribofuranosyl)-8H-furo[2',3':4,5]pyrrolo[2,3-d]pyrimidin-4-amine,
4-(furan-2-yl)-8-(β-D-ribofuranosyl)-8H-furo[2',3':4,5]pyrrolo[2,3-d]pyrimidine,
4-(furan-3-yl)-8-(β-D-ribofuranosyl)-8H-furo [2',3':4,5]pyrrolo[2,3-d]pyrimidine,
4-(benzofuran-2-yl)-8-(β-D-ribofuranosyl)-8H-furo[2',3':4,5]pyrrolo[2,3-d]pyrimidine,
N,N-dimethyl-8-(β-D-ribofuranosyl)-8H-furo[2',3':4,5]pyrrolo[2,3-d]pyrimidin-4-amine, 4,5-dimethyl-8-(β-D-ribofuranosyl)-5,8-dihydropyrrolo[2',3':4,5]pyrrolo[2,3-d]pyrimidine, 4-methoxy-5-methyl-8-(β-D-ribofuranosyl)-5,8-dihydropyrrolo[2',3':4,5]pyrrolo[2,3-d]pyrimidine, 5-methyl-4-(methylsulfanyl)-8-(β-D-ribofuranosyl)-5,8-dihydropyrrolo[2',3':4,5]pyrrolo[2,3-d]pyrimidine, 5-methyl-8-(β-D-ribofuranosyl)-5,8-dihydropyrrolo[2',3':4,5]pyrrolo[2,3-d]pyrimidin-4-amine, 4-(furan-2-yl)-5-methyl-8-(β-D-ribofuranosyl)-5,8-dihydropyrrolo[2',3':4,5]pyrrolo[2,3-d]pyrimidine, 4-(furan-3-yl)-5-methyl-8-(β-D-ribofuranosyl)-5,8-dihydropyrrolo[2',3':4,5]pyrrolo[2,3-d]pyrimidine, 4-(benzofuran-2-yl)-5-methyl-8-(β-D-ribofuranosyl)-5,8-dihydropyrrolo[2',3':4,5]pyrrolo[2,3-d]pyrimidine, N,N,5-trimethyl-8-(β-D-ribofuranosyl)-5,8-dihydropyrrolo[2',3':4,5]pyrrolo[2,3-d]pyrimidin-4-amine, and 4-chloro-5-methyl-8-(β-D-ribofuranosyl)-5,8-dihydropyrrolo[2',3':4,5]pyrrolo[2,3-d]pyrimidine.

5. A method of inhibition of pathological cell proliferation comprising the step of providing 4-substituted heteropentadieno-pyrrolopyrimidine ribonucleosides of general formula I according to claim 1 to a subject in need thereof.

6. A method of treatment of tumor diseases selected from the group consisting of lung cancer, leukemia, colon cancer and bone cancer comprising the step of providing 4-substituted heteropentadieno-pyrrolopyrimidine ribonucleosides of general formula I according to claim 1 to a subject in need thereof.

7. A pharmaceutical composition characterised in that it comprises a therapeutically effective amount of at least one compound of general formula I according to claim 1, and optionally also at least one pharmaceutically acceptable carrier, filles and/or excipient.

8. A pharmaceutical composition according to claim 7 for use in inhibition of pathological cell proliferation of tumor/non-tumor origin and/or for treatment of tumor/non tumor disease associated with cell hyperproliferation.

* * * * *